US011107591B1

(12) United States Patent
Mason

(10) Patent No.: US 11,107,591 B1
(45) Date of Patent: Aug. 31, 2021

(54) METHOD AND SYSTEM FOR DESCRIBING AND RECOMMENDING OPTIMAL TREATMENT PLANS IN ADAPTIVE TELEMEDICAL OR OTHER CONTEXTS

(71) Applicant: ROM TECHNOLOGIES, INC., Brookfield, CT (US)

(72) Inventor: Steven Mason, Las Vegas, NV (US)

(73) Assignee: ROM Technologies, Inc., Brookfield, CT (US)

( * ) Notice: Subject to any disclaimer, the term of this patent is extended or adjusted under 35 U.S.C. 154(b) by 0 days.

(21) Appl. No.: 16/856,985

(22) Filed: Apr. 23, 2020

(51) Int. Cl.
| | | |
|---|---|---|
| *G16H 80/00* | (2018.01) | |
| *G16H 40/67* | (2018.01) | |
| *G06F 40/205* | (2020.01) | |
| *G16H 10/60* | (2018.01) | |
| *G06N 3/02* | (2006.01) | |
| *G16H 20/60* | (2018.01) | |
| *G16H 20/70* | (2018.01) | |

(Continued)

(52) U.S. Cl.
CPC ........... *G16H 80/00* (2018.01); *G06F 40/205* (2020.01); *G06N 3/02* (2013.01); *G06N 20/00* (2019.01); *G16H 10/60* (2018.01); *G16H 20/10* (2018.01); *G16H 20/60* (2018.01); *G16H 20/70* (2018.01); *G16H 40/67* (2018.01)

(58) Field of Classification Search
CPC ........ G16H 10/00; G16H 10/40; G16H 15/00; G16H 20/00; G16H 20/10; G16H 20/13; G16H 20/17; G16H 30/00; G16H 40/00; G16H 50/00; G16H 70/00; G16H 80/00; G16H 40/67; G16H 10/60; G16H 20/60; G16H 20/70; G06N 20/00; G06N 3/02; G06F 40/205

USPC .................................................. 705/2, 3, 20
See application file for complete search history.

(56) References Cited

U.S. PATENT DOCUMENTS 6,182,029 B1 * 1/2001 Friedman .............. G06F 40/205
704/9
6,413,190 B1 7/2002 Wood et al.
(Continued)

FOREIGN PATENT DOCUMENTS

| CA | 2698078 A1 | 3/2010 |
|---|---|---|
| CN | 112603295 A | 2/2003 |
| WO | 2019204876 A1 | 4/2019 |

*Primary Examiner* — Robert W Morgan
*Assistant Examiner* — Charles P Coleman
(74) *Attorney, Agent, or Firm* — Dickinson Wright, PLLC; Stephen A. Mason; Jonathan H. Harder

(57) ABSTRACT

A method is disclosed for providing, by an artificial intelligence engine, an optimal treatment plan to use with a treatment apparatus. The method includes receiving, from a data source, clinical information pertaining to results of using the treatment apparatus to perform particular treatment plans for people having certain characteristics. The clinical information has a first data format. The method also includes translating a portion of the clinical information from the first data format to a medical description language used by the artificial intelligence engine, determining, based on the portion of the clinical information described by the medical description language and a plurality of characteristics pertaining to a patient, the optimal treatment plan for the patient to follow using the treatment apparatus to achieve a desired result, and providing the optimal treatment plan to be presented on a computing device of a medical professional.

20 Claims, 10 Drawing Sheets

(51) Int. Cl.
  *G06N 20/00*   (2019.01)
  *G16H 20/10*   (2018.01)

(56) References Cited

U.S. PATENT DOCUMENTS

| | | |
|---|---|---|
| 6,491,649 B1 | 12/2002 | Ombrellaro |
| 7,169,085 B1 | 1/2007 | Killin et al. |
| 7,209,886 B2 | 4/2007 | Kimmel |
| 7,974,689 B2 | 7/2011 | Volpe et al. |
| 8,751,264 B2 | 6/2014 | Beraja et al. |
| 8,823,448 B1 | 9/2014 | Shen |
| 9,311,789 B1 | 4/2016 | Gwin |
| 9,919,198 B2 | 3/2018 | Romeo et al. |
| 9,939,784 B1 | 4/2018 | Berardinelli |
| 10,130,298 B2 | 11/2018 | Mokaya et al. |
| 10,424,033 B2 | 9/2019 | Romeo |
| 2003/0036683 A1 | 2/2003 | Kehr et al. |
| 2020/0401224 A1 | 2/2003 | Ronald |
| 2006/0064329 A1 | 3/2006 | Abolfathi et al. |
| 2009/0011907 A1 | 1/2009 | Radow et al. |
| 2009/0070138 A1 | 3/2009 | Langheier et al. |
| 2010/0268304 A1 | 10/2010 | Matos |
| 2011/0172059 A1 | 7/2011 | Watterson et al. |
| 2011/0218814 A1 | 9/2011 | Coats |
| 2012/0065987 A1 | 3/2012 | Farooq et al. |
| 2012/0190502 A1 | 7/2012 | Paulus et al. |
| 2012/0310667 A1* | 12/2012 | Altman .................. G06Q 50/24 705/3 |
| 2013/0123667 A1 | 5/2013 | Komatireddy et al. |
| 2013/0296987 A1 | 11/2013 | Rogers et al. |
| 2014/0006042 A1 | 1/2014 | Keefe et al. |
| 2014/0188009 A1 | 7/2014 | Lange et al. |
| 2014/0194250 A1 | 7/2014 | Reich et al. |
| 2014/0257837 A1 | 9/2014 | Walker et al. |
| 2014/0322686 A1 | 10/2014 | Kang |
| 2015/0088544 A1 | 3/2015 | Goldberg |
| 2015/0161331 A1* | 6/2015 | Oleynik .................. G16H 50/70 705/3 |
| 2015/0339442 A1* | 11/2015 | Oleynik .................. G16H 50/70 705/3 |
| 2016/0140319 A1 | 5/2016 | Stark et al. |
| 2016/0166881 A1 | 6/2016 | Ridgel et al. |
| 2016/0275259 A1 | 9/2016 | Nolan et al. |
| 2016/0302721 A1 | 10/2016 | Wiedenhoefer et al. |
| 2017/0004260 A1 | 1/2017 | Moturu et al. |
| 2017/0143261 A1 | 5/2017 | Wiedenhoefer et al. |
| 2017/0147789 A1 | 5/2017 | Wiedenhoefer et al. |
| 2017/0181698 A1 | 6/2017 | Wiedenhoefer et al. |
| 2017/0243028 A1 | 8/2017 | LaFever et al. |
| 2017/0278209 A1 | 9/2017 | Olsen et al. |
| 2017/0300654 A1 | 10/2017 | Stein et al. |
| 2017/0329917 A1 | 11/2017 | McRaith et al. |
| 2017/0344726 A1 | 11/2017 | Duffy et al. |
| 2017/0360586 A1 | 12/2017 | Dempers et al. |
| 2018/0052962 A1* | 2/2018 | Van Der Koijk ...... G16H 50/20 |
| 2018/0085615 A1 | 3/2018 | Astolfi et al. |
| 2018/0102190 A1* | 4/2018 | Hogue .................. G16H 50/20 |
| 2018/0240552 A1* | 8/2018 | Tuyl ........................ G06N 5/02 |
| 2018/0271432 A1 | 9/2018 | Auchinleck et al. |
| 2018/0280784 A1 | 10/2018 | Romeo et al. |
| 2018/0330824 A1 | 11/2018 | Athey et al. |
| 2019/0019578 A1 | 1/2019 | Vaccaro |
| 2019/0066832 A1 | 2/2019 | Kang et al. |
| 2019/0167988 A1 | 6/2019 | Shahriari et al. |
| 2020/0143922 A1 | 5/2020 | Chekroud et al. |
| 2020/0151595 A1 | 5/2020 | Jayalath et al. |
| 2020/0152339 A1 | 5/2020 | Pulitzer et al. |
| 2020/0160198 A1 | 5/2020 | Reeves et al. |
| 2020/0176098 A1* | 6/2020 | Lucas .................. G16H 15/00 |
| 2020/0293712 A1* | 9/2020 | Potts ........................ G16H 10/60 |

\* cited by examiner

700

EFFECT OF USING TREATMENT PLAN FOR HIP OSTEOARTHRITIS PAIN

Results

Six trials met the inclusion criteria (2,000 subjects), 7 of which combined hip and knee osteoarthritis (OA). In comparing exercise treatment versus control, we found a beneficial effect of exercise with an effect size of −0.4, but with high heterogeneity ($I^2 = 75\%$) among trials. The treatment plan XYZ in the study included similar treatment protocols specifying using a range of motion (ROM) treatment apparatus by people having similar characteristics (diabetic, hip osteoarthritis).

Conclusion

Therapeutic exercise using the treatment plan with the treatment apparatus is an efficacious treatment for hip OA.

SERVER 30

702

MEDICAL DESCRIPTION LANGUAGE
```

<trials>6</trials>
    <subjects>2000</subjects>
    <treatment plan>XYZ</treatment plan>
    <treatment apparatus>ROM</treatment apparatus>
    <subject characteristics>diabetic, hip osteoarthritis</subject characteristics>
    <conclusion>efficacious</conclusion>

METHOD AND SYSTEM FOR DESCRIBING AND RECOMMENDING OPTIMAL TREATMENT PLANS IN ADAPTIVE TELEMEDICAL OR OTHER CONTEXTS

BACKGROUND

Remote medical assistance, or telemedicine, may aid a patient in performing various aspects of a rehabilitation regimen for a body part. The patient may use a patient interface in communication with an assistant interface for receiving the remote medical assistance via audio and/or audiovisual communications.

SUMMARY

In one embodiment, a method is disclosed for providing, by an artificial intelligence engine, an optimal treatment plan to use with a treatment apparatus. The method includes receiving, from a data source, clinical information pertaining to results of using the treatment apparatus to perform particular treatment plans for people having certain characteristics. The clinical information has a first data format. The method also includes translating a portion of the clinical information from the first data format to a medical description language used by the artificial intelligence engine, determining, based on the portion of the clinical information described by the medical description language and a plurality of characteristics pertaining to a patient, the optimal treatment plan for the patient to follow using the treatment apparatus to achieve a desired result, and providing the optimal treatment plan to be presented on a computing device of a medical professional.

In one embodiment, a system includes a memory storing instructions and a processing device communicatively coupled to the memory. The processing device executes the instructions to perform any of the methods, operations, or steps described herein.

In one embodiment, a tangible, non-transitory computer-readable medium stores instructions that, when executed, cause a processing device to perform any of the methods, operations, or steps described herein.

BRIEF DESCRIPTION OF THE DRAWINGS

For a detailed description of example embodiments, reference will now be made to the accompanying drawings in which:

FIG. 7 shows an example embodiment of a server translating clinical information into a medical description language for processing by an artificial intelligence engine according to the present disclosure;

NOTATION AND NOMENCLATURE

Figure 1:
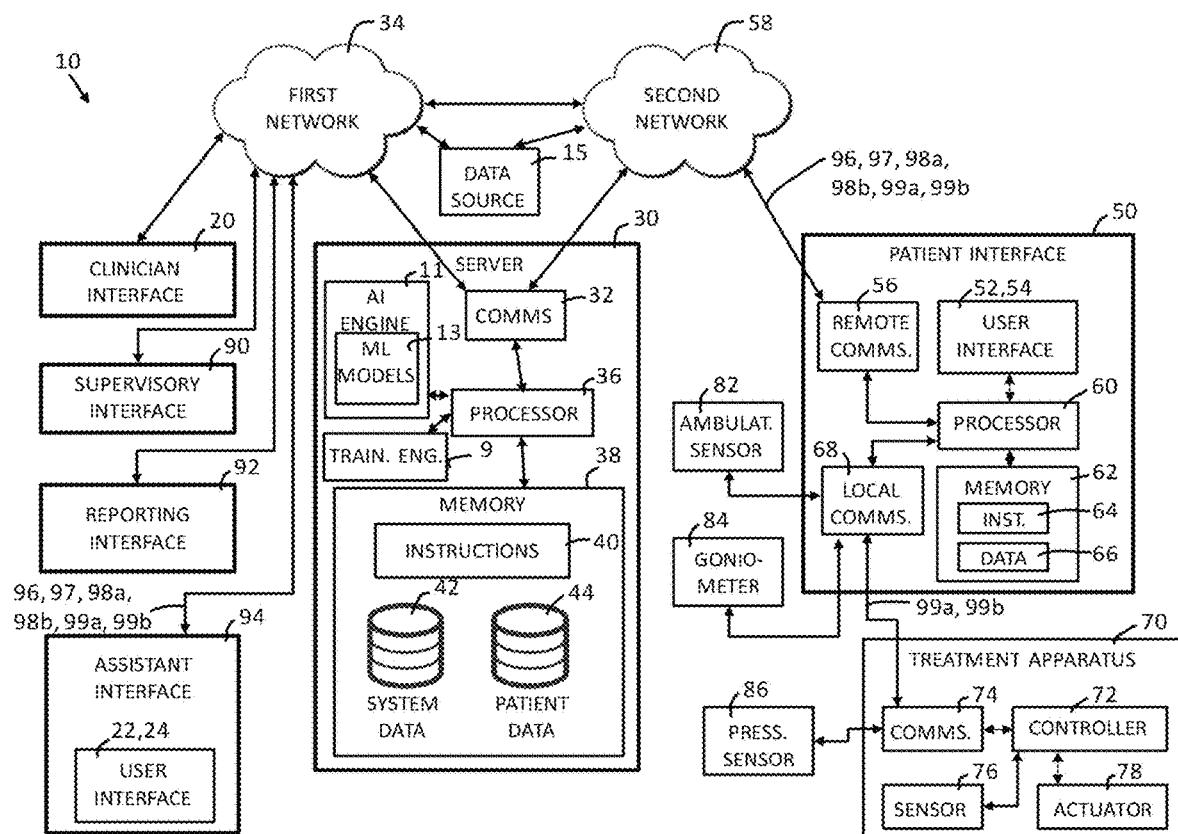
FIG. 1 shows a block diagram of an embodiment of a computer implemented system for managing a treatment plan according to the present disclosure.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection or through an indirect connection via other devices and connections.

The terminology used herein is for the purpose of describing particular example embodiments only, and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer, or section from another region, layer, or section. Terms such as "first," "second," and other numerical terms, when used herein, do not imply a sequence or order unless clearly indicated by the context. Thus, a first element, component, region, layer, or section discussed below could be termed a second element, component, region, layer, or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Spatially relative terms, such as "inner," "outer," "beneath," "below," "lower," "above," "upper," "top," "bottom," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

DETAILED DESCRIPTION

The following discussion is directed to various embodiments of the present disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Determining an optimal treatment plan for a patient having certain characteristics (e.g., demographic; geographic; diagnostic; measurement- or test-based; medically historic; etiologic; cohort-associative; differentially diagnostic; surgical, physically therapeutic, pharmacologic and other treatment(s) recommended; etc.) may be a technically challenging problem. For example, a multitude of information may be considered when determining a treatment plan, which may result in inefficiencies and inaccuracies in the treatment plan selection process. In a rehabilitative setting, some of the multitude of information considered may include a type of injury of the patient, types of available medical procedures to perform, treatment regimens, medication regimens, and the characteristics of the patient. The characteristics of the patient may be vast, and may include medications of the patient, previous injuries of the patient, previous medical procedures performed on the patient, measurements (e.g., body fat, weight, etc.) of the patient, allergies of the patient, medical conditions of the patient, historical information of the patient, vital signs (e.g., temperature, blood pressure, heart rate) of the patient, symptoms of the patient, familial medical information of the patient, and the like.

Further, in addition to the information described above, it may be desirable to consider additional historical information, such as clinical information pertaining to results of treatment plans performed using a treatment apparatus on other people. The clinical information may include clinical studies, clinical trials, evidence-based guidelines, journal articles, meta-analyses, and the like. The clinical information may be written by people having certain professional degrees (e.g., medical doctor, osteopathic doctor, physical therapist, etc.), certifications, etc. The clinical information may be retrieved from any suitable data source.

In some embodiments, the clinical information may describe people seeking treatment for a particular ailment (e.g., injury, disease, any applicable medical condition, etc.). The clinical information may describe that certain results are obtained when the people perform or have performed on them particular treatment plans (e.g., medical procedures, treatment protocols using treatment apparatuses, medication regimens, diet regimens, etc.). The clinical information may also include the particular characteristics of the people described. Direct or indirect reference may be made to values of the characteristics therein. It may be desirable to compare the characteristics of the patient with the characteristics of the people in the clinical information to determine what an optimal treatment plan for the patient may be such that the patient can obtain a desired result. Processing this historical information may be computationally taxing, inefficient, and/or infeasible using conventional techniques.

Accordingly, embodiments of the present disclosure pertain to recommending optimal treatment plans using real-time and historical data correlations involving patient cohort-equivalent databases. In some embodiments, an artificial intelligence engine may be trained to recommend the optimal treatment plan based on characteristics of the patient and the clinical information. For example, the artificial intelligence engine may be trained to match a pattern between the characteristics of the patient and the people in various clinical information. Based on the pattern, the artificial intelligence engine may generate a treatment plan for the patient, where such treatment plan produced a desired result in the clinical information for a similarly matched person or similarly matched people. In that sense, the treatment plan generated may be "optimal" based on the desired result (e.g., speed, efficacy, both speed and efficacy, life expectancy, etc.). In other words, based on the characteristics of the patient, in order to obtain the desired result, there may be certain medical procedures, certain medications, certain rehabilitative exercises, and so forth that should be included in an optimal treatment plan to obtain the desired result.

Depending on what result is desired, the artificial intelligence engine may be trained to output several optimal or optimized treatment plans. For example, one result may include recovering to a threshold level (e.g., 75% range of motion) in a fastest amount of time, while another result may include fully recovering (e.g., 100% range of motion) regardless of the amount of time. The clinical information may indicate a first treatment plan provides the first result for people with characteristics similar to the patient's, and a second treatment plan provides the second result for people with characteristics similar to the patient.

Further, the artificial intelligence engine may also be trained to output treatment plans that are not optimal (referred to as "ruled-out treatment plans") for the patient. For example, if a patient has diabetes, a particular medication may not be approved or suitable for the patient and that medication may be flagged in the ruled-out treatment plan for the patient.

As discussed above, processing patient and clinical information in real-time may, due to the sheer amount of data to process, be infeasible using conventional techniques. Accordingly, in some embodiments, the received clinical information and/or patient information may be translated into a medical description language. The medical description language may refer to an encoding configured to be efficiently processed by the artificial intelligence engine. For example, a clinical trial may be received and parsed, optionally with the addition of an attribute grammar; and then keywords pertaining to target information may be searched for. The values of the target information may be identified. A canonical format defined by the medical description language may be defined and/or generated, where the canonical format includes tags identifying the values of the target information and, optionally, tags implementing an attribute grammar for the medical description language.

The medical description language may be extensible and include any property of an object-oriented or artificial intelligence programming language. The medical description language may define other methods or procedures. The medical description language may implement the concept of "objects", which can contain data, in the form of fields (often known as attributes or properties), and code, in the form of procedures (often known as methods). The medical description language may encapsulate data and functions that manipulate the data to protect them from interference and misuse. The medical description language may also implement data hiding or obscuring, which prevents certain aspects of the data or functions from being accessible to another component. The medical description language may implement inheritance, which arranges components as "is a type of" relationships, where a first component may be a type of a second component and the first component inherits the functions and data of the second component. The medical description language may also implement polymorphism, which is the provision of a single interface to components of different types.

The clinical information may be translated to the medical description language prior to the artificial intelligence engine determining the optimal treatment plans and/or ruled-out treatment plans. The artificial intelligence engine may be trained by using the medical description language representing the clinical information, such that the artificial intelligence engine is able to more efficiently determine the optimal treatment plans instead of using initial data formats in which the clinical information is received. Further, the artificial intelligence engine may continuously or continually receive the clinical information and include the clinical information in training data to update the artificial intelligence engine.

In some embodiments, the optimal treatment plans and/or ruled-out treatment plans may be presented to a medical professional. The medical professional may select a particular optimal treatment plan for the patient to cause that treatment plan to be transmitted to the patient. In some embodiments, to facilitate telehealth or telemedicine applications, including remote diagnoses, determination of treatment plans and rehabilitative and/or pharmacologic prescriptions, the artificial intelligence engine may receive and/or operate distally from the source of the clinical information and/or distally from the patient. In such cases, the recommended treatment plans and/or ruled-out treatment plans may be presented during a telemedicine or telehealth session on a user interface of a computing device of a medical professional simultaneously with a video of the patient in real-time. The video may also be accompanied by audio, text and other multimedia information. Real-time may refer to less than 2 seconds.

Presenting the treatment plans generated by the artificial intelligence engine concurrently with a presentation of the patient video may provide an enhanced user interface because the medical professional may continue to visually and/or otherwise communicate with the patient while also reviewing the treatment plans on the same user interface. The enhanced user interface may improve the medical professional's experience using the computing device and may encourage the medical professional to reuse the user interface. Such a technique may also reduce computing resources (e.g., processing, memory, network) because the medical professional does not have to switch to another user interface screen and enter a query for a treatment plan to recommend based on the characteristics of the patient. The artificial intelligence engine provides, dynamically on the fly, the optimal treatment plans and ruled-out treatment plans.

In some embodiments, the treatment apparatus may be adaptive and/or personalized because its properties, configurations, and positions may be adapted to the needs of a particular patient. For example, the pedals may be dynamically adjusted on the fly (e.g., via a telemedicine session or based on programmed configurations in response to certain measurements being detected) to increase or decrease a range of motion to comply with a treatment plan designed for the user. Such adaptive nature may improve the results of recovery for a patient.

FIG. 1 shows a block diagram of a computer-implemented system 10, hereinafter called "the system" for managing a treatment plan. Managing the treatment plan may include using an artificial intelligence engine to recommend optimal treatment plans and/or provide ruled-out treatment plans that should not be recommended to a patient. A treatment plan may include one or more treatment protocols, and each treatment protocol includes one or more treatment sessions. Each treatment session comprises several session periods, with each session period including a particular activity for treating the body part of the patient. For example, a treatment plan for post-operative rehabilitation after a knee surgery may include an initial treatment protocol with twice daily stretching sessions for the first 3 days after surgery and a more intensive treatment protocol with active exercise sessions performed 4 times per day starting 4 days after surgery. A treatment plan may also include information pertaining to a medical procedure to perform on the patient, a treatment protocol for the patient using a treatment apparatus, a diet regimen for the patient, a medication regimen for the patient, a sleep regimen for the patient, additional regimens, or some combination thereof.

The system 10 also includes a server 30 configured to store and to provide data related to managing the treatment plan. The server 30 may include one or more computers and may take the form of a distributed and/or virtualized computer or computers. The server 30 also includes a first communication interface 32 configured to communicate with the clinician interface 20 via a first network 34. In some embodiments, the first network 34 may include wired and/or wireless network connections such as Wi-Fi, Bluetooth, ZigBee, Near-Field Communications (NFC), cellular data network, etc. The server 30 includes a first processor 36 and a first machine-readable storage memory 38, which may be called a "memory" for short, holding first instructions 40 for performing the various actions of the server 30 for execution by the first processor 36. The server 30 is configured to store data regarding the treatment plan. For example, the memory 38 includes a system data store 42 configured to hold system data, such as data pertaining to treatment plans for treating one or more patients. The server 30 is also configured to store data regarding performance by a patient in following a treatment plan. For example, the memory 38 includes a patient data store 44 configured to hold patient data, such as data pertaining to the one or more patients, including data representing each patient's performance within the treatment plan.

In addition, the characteristics of the people, the treatment plans followed by the people, the level of compliance with the treatment plans, and the results of the treatment plans may use correlations and other statistical or probabilistic measures to partition the treatment plans into different patient cohort-equivalent databases in the patient data store 44. For example, the data for a first cohort of first patients having a first similar injury, a first similar medical condition, a first similar medical procedure performed, a first treatment plan followed by the first patient, and a first result of the treatment plan may be stored in a first patient database. The data for a second cohort of second patients having a second similar injury, a second similar medical condition, a second similar medical procedure performed, a second treatment plan followed by the second patients, and a second result of the treatment plan may be stored in a second patient database. Any combination of characteristics may be used to separate the cohorts of patients. In some embodiments, the different cohorts of patients may be stored in different partitions or volumes of the same database.

This characteristic data, treatment plan data, and results data may be obtained from clinical information that describes the characteristics of people who performed certain treatment plans and the results of those treatment plans. The characteristic data, treatment plan data, and results data may be correlated in the patient-cohort databases in the patient data store 44. The characteristics of the people may include medications prescribed to the people, injuries of the people, medical procedures performed on the people, measurements of the people, allergies of the people, medical conditions of the people, historical information of the people, vital signs of the people, symptoms of the people, familial medical information of the people, other information of the people, or some combination thereof.

In addition to the historical information about other people stored in the patient cohort-equivalent databases, real-time information based on the current patient's characteristics about a current patient being treated may be stored in an appropriate patient cohort-equivalent database. The characteristics of the patient may include medications of the patient, injuries of the patient, medical procedures performed on the patient, measurements of the patient, allergies of the patient, medical conditions of the patient, historical information of the patient, vital signs of the patient, symptoms of the patient, familial medical information of the patient, other information of the patient, or some combination thereof.

In some embodiments, the server 30 may execute an artificial intelligence (AI) engine 11 that uses one or more machine learning models 13 to perform at least one of the embodiments disclosed herein. The server 30 may include a training engine 9 capable of generating the one or more machine learning models 13. The machine learning models 13 may be trained to generate and recommend optimal treatment plans using real-time and historical data correlations involving patient cohort-equivalents, among other things. The one or more machine learning models 13 may be generated by the training engine 9 and may be implemented in computer instructions executable by one or more processing devices of the training engine 9 and/or the servers 30. To generate the one or more machine learning models 13, the training engine 9 may train the one or more machine learning models 13. The one or more machine learning models 13 may be used by the artificial intelligence engine 11.

The training engine 9 may be a rackmount server, a router computer, a personal computer, a portable digital assistant, a smartphone, a laptop computer, a tablet computer, a netbook, a desktop computer, an Internet of Things (IoT) device, any other desired computing device, or any combination of the above. The training engine 9 may be cloud-based or a real-time software platform, and it may include privacy software or protocols, and/or security software or protocols.

To train the one or more machine learning models 13, the training engine 9 may use a training data set of a corpus of keywords representing target information to identify clinical information. The training data set may also include a corpus of clinical information (e.g., clinical trials, meta-analyses, evidence-based guidelines, journal articles, etc.) having a first data format. The clinical information may include characteristics of people, treatment plans followed by the people, and results of the treatment plans, among other things. The training data set may also include medical description language examples that include tags for target information, telemedical information and values embedded with the tags. The one or more machine learning models may be trained to translate the clinical information from the first data format to the machine description language having a canonical (e.g., tag-value pair and/or attribute grammar) format. The training may be performed by identifying the keywords of the target information, identifying values for the keywords, and generating the canonical value including tags for the target information and the values for the target information.

The one or more machine learning models 13 may also be trained to translate characteristics of patients received in real-time (e.g., from an electronic medical records (EMR) system) to the medical description language to store in appropriate patient cohort-equivalent databases. The one or more machine learning models 13 may be trained to match patterns of characteristics of a patient described by the medical description language with characteristics of other people described by the medical description language that represents the clinical information. In some embodiments, the medical description language representing the clinical information may be stored in the various patient cohort-equivalent databases of the patient data store 44. Accordingly, in some embodiments, the one or more machine learning models 13 may access the patient cohort-equivalent databases when being trained or when recommending optimal treatment plans for a patient. Computing resources, efficiency of processing, accuracy and error minimization may be enhanced using the medical description language in the canonical format, as opposed to full bodies of text and/or EMR records. In particular, accuracy may be improved and errors may be minimized through the use of a formal medical description language that may be parsed to have one meaning, while informal descriptions may result in more than one, potentially semantically overloaded and unresolvable meanings.

Different machine learning models 13 may be trained to recommend different optimal treatment plans for different desired results. For example, one machine learning model may be trained to recommend optimal treatment plans for most effective recovery, while another machine learning model may be trained to recommend optimal treatment plans based on speed of recovery.

Using training data that includes training inputs and corresponding target outputs, the one or more machine learning models 13 may refer to model artifacts created by the training engine 9. The training engine 9 may find patterns in the training data wherein such patterns map the training input to the target output, and generate the machine learning models 13 that capture these patterns. In some embodiments, the artificial intelligence engine 11, the database 33, and/or the training engine 9 may reside on another component (e.g., assistant interface 94, clinician interface 20, etc.) depicted in FIG. 1.

As described in more detail below, the one or more machine learning models 13 may comprise, e.g., a single level of linear or non-linear operations (e.g., a support vector machine [SVM]) or the machine learning models 13 may be a deep network, i.e., a machine learning model comprising multiple levels of non-linear operations. Examples of deep networks are neural networks including generative adversarial networks, convolutional neural networks, recurrent neural networks with one or more hidden layers, and fully connected neural networks (e.g., each neuron may transmit its output signal to the input of the remaining neurons, as well as to itself). For example, the machine learning model may include numerous layers and/or hidden layers that perform calculations (e.g., dot products) using various neurons.

The system 10 also includes a patient interface 50 configured to communicate information to a patient and to receive feedback from the patient. Specifically, the patient interface includes an input device 52 and an output device 54, which may be collectively called a patient user interface 52, 54. The input device 52 may include one or more devices, such as a keyboard, a mouse, a touch screen input, a gesture sensor, and/or a microphone and processor configured for voice recognition. The output device 54 may take one or more different forms including, for example, a computer monitor or display screen on a tablet, smartphone, or a smart watch. The output device 54 may include other hardware and/or software components such as a projector, virtual reality capability, augmented reality capability, etc. The output device 54 may incorporate various different visual, audio, or other presentation technologies. For example, the output device 54 may include a non-visual display, such as an audio signal, which may include spoken language and/or other sounds such as tones, chimes, and/or melodies, which may signal different conditions and/or directions. The output device 54 may comprise one or more different display screens presenting various data and/or interfaces or controls for use by the patient. The output device 54 may include graphics, which may be presented by a web-based interface and/or by a computer program or application (App.).

As shown in FIG. 1, the patient interface 50 includes a second communication interface 56, which may also be called a remote communication interface configured to communicate with the server 30 and/or the clinician interface 20 via a second network 58. In some embodiments, the second network 58 may include a local area network (LAN), such as an Ethernet network. In some embodiments, the second network 58 may include the Internet, and communications between the patient interface 50 and the server 30 and/or the clinician interface 20 may be secured via encryption, such as, for example, by using a virtual private network (VPN). In some embodiments, the second network 58 may include wired and/or wireless network connections such as Wi-Fi, Bluetooth, ZigBee, Near-Field Communications (NFC), cellular data network, etc. In some embodiments, the second network 58 may be the same as and/or operationally coupled to the first network 34.

The patient interface 50 includes a second processor 60 and a second machine-readable storage memory 62 holding second instructions 64 for execution by the second processor 60 for performing various actions of patient interface 50. The second machine-readable storage memory 62 also includes a local data store 66 configured to hold data, such as data pertaining to a treatment plan and/or patient data, such as data representing a patient's performance within a treatment plan. The patient interface 50 also includes a local communication interface 68 configured to communicate with various devices for use by the patient in the vicinity of the patient interface 50. The local communication interface 68 may include wired and/or wireless communications. In some embodiments, the local communication interface 68 may include a local wireless network such as Wi-Fi, Bluetooth, ZigBee, Near-Field Communications (NFC), cellular data network, etc.

The system 10 also includes a treatment apparatus 70 configured to be manipulated by the patient and/or to manipulate a body part of the patient for performing activities according to the treatment plan. In some embodiments, the treatment apparatus 70 may take the form of an exercise and rehabilitation apparatus configured to perform and/or to aid in the performance of a rehabilitation regimen, which may be an orthopedic rehabilitation regimen, and the treatment includes rehabilitation of a body part of the patient, such as a joint or a bone or a muscle group. The body part may include, for example, a spine, a hand, a foot, a knee, or a shoulder. The body part may include a part of a joint, a bone, or a muscle group, such as one or more vertebrae, a tendon, or a ligament. As shown in FIG. 1, the treatment apparatus 70 includes a controller 72, which may include one or more processors, computer memory, and/or other components. The treatment apparatus 70 also includes a fourth communication interface 74 configured to communicate with the patient interface 50 via the local communication interface 68. The treatment apparatus 70 also includes one or more internal sensors 76 and an actuator 78, such as a motor. The actuator 78 may be used, for example, for moving the patient's body part and/or for resisting forces by the patient.

The internal sensors 76 may measure one or more operating characteristics of the treatment apparatus 70 such as, for example, a force a position, a speed, and/or a velocity. In some embodiments, the internal sensors 76 may include a position sensor configured to measure at least one of a linear motion or an angular motion of a body part of the patient. For example, an internal sensor 76 in the form of a position sensor may measure a distance that the patient is able to move a part of the treatment apparatus 70, where such distance may correspond to a range of motion that the patient's body part is able to achieve. In some embodiments, the internal sensors 76 may include a force sensor configured to measure a force applied by the patient. For example, an internal sensor 76 in the form of a force sensor may measure a force or weight the patient is able to apply, using a particular body part, to the treatment apparatus 70.

The system 10 shown in FIG. 1 also includes an ambulation sensor 82, which communicates with the server 30 via the local communication interface 68 of the patient interface 50. The ambulation sensor 82 may track and store a number of steps taken by the patient. In some embodiments, the ambulation sensor 82 may take the form of a wristband, wristwatch, or smart watch. In some embodiments, the ambulation sensor 82 may be integrated within a phone, such as a smartphone.

The system 10 shown in FIG. 1 also includes a goniometer 84, which communicates with the server 30 via the local communication interface 68 of the patient interface 50. The goniometer 84 measures an angle of the patient's body part. For example, the goniometer 84 may measure the angle of flex of a patient's knee or elbow or shoulder.

The system 10 shown in FIG. 1 also includes a pressure sensor 86, which communicates with the server 30 via the local communication interface 68 of the patient interface 50. The pressure sensor 86 measures an amount of pressure or weight applied by a body part of the patient. For example, pressure sensor 86 may measure an amount of force applied by a patient's foot when pedaling a stationary bike.

The system 10 shown in FIG. 1 also includes a supervisory interface 90 which may be similar or identical to the clinician interface 20. In some embodiments, the supervisory interface 90 may have enhanced functionality beyond what is provided on the clinician interface 20. The supervisory interface 90 may be configured for use by a person having responsibility for the treatment plan, such as an orthopedic surgeon.

The system 10 shown in FIG. 1 also includes a reporting interface 92 which may be similar or identical to the clinician interface 20. In some embodiments, the reporting interface 92 may have less functionality from what is provided on the clinician interface 20. For example, the reporting interface 92 may not have the ability to modify a treatment plan. Such a reporting interface 92 may be used, for example, by a biller to determine the use of the system 10 for billing purposes. In another example, the reporting interface 92 may not have the ability to display patient identifiable information, presenting only pseudonymized data and/or anonymized data for certain data fields concerning a data subject and/or for certain data fields concerning a quasi-identifier of the data subject. Such a reporting interface 92 may be used, for example, by a researcher to determine various effects of a treatment plan on different patients.

The system 10 includes an assistant interface 94 for an assistant, such as a doctor, a nurse, a physical therapist, or a technician, to remotely communicate with the patient interface 50 and/or the treatment apparatus 70. Such remote communications may enable the assistant to provide assistance or guidance to a patient using the system 10. More specifically, the assistant interface 94 is configured to communicate a telemedicine signal 96, 97, 98a, 98b, 99a, 99b with the patient interface 50 via a network connection such as, for example, via the first network 34 and/or the second network 58. The telemedicine signal 96, 97, 98a, 98b, 99a, 99b comprises one of an audio signal 96, an audiovisual signal 97, an interface control signal 98a for controlling a function of the patient interface 50, an interface monitor signal 98b for monitoring a status of the patient interface 50, an apparatus control signal 99a for changing an operating parameter of the treatment apparatus 70, and/or an apparatus monitor signal 99b for monitoring a status of the treatment apparatus 70. In some embodiments, each of the control signals 98a, 99a may be unidirectional, conveying commands from the assistant interface 94 to the patient interface 50. In some embodiments, in response to successfully receiving a control signal 98a, 99a and/or to communicate successful and/or unsuccessful implementation of the requested control action, an acknowledgement message may be sent from the patient interface 50 to the assistant interface 94. In some embodiments, each of the monitor signals 98b, 99b may be unidirectional, status-information commands from the patient interface 50 to the assistant interface 94. In some embodiments, an acknowledgement message may be sent from the assistant interface 94 to the patient interface 50 in response to successfully receiving one of the monitor signals 98b, 99b.

In some embodiments, the patient interface 50 may be configured as a pass-through for the apparatus control signals 99a and the apparatus monitor signals 99b between the treatment apparatus 70 and one or more other devices, such as the assistant interface 94 and/or the server 30. For example, the patient interface 50 may be configured to transmit an apparatus control signal 99a in response to an apparatus control signal 99a within the telemedicine signal 96, 97, 98a, 98b, 99a, 99b from the assistant interface 94.

In some embodiments, the assistant interface 94 may be presented on a shared physical device as the clinician interface 20. For example, the clinician interface 20 may include one or more screens that implement the assistant interface 94. Alternatively or additionally, the clinician interface 20 may include additional hardware components, such as a video camera, a speaker, and/or a microphone, to implement aspects of the assistant interface 94.

In some embodiments, one or more portions of the telemedicine signal 96, 97, 98a, 98b, 99a, 99b may be generated from a prerecorded source (e.g., an audio recording, a video recording, or an animation) for presentation by the output device 54 of the patient interface 50. For example, a tutorial video may be streamed from the server 30 and presented upon the patient interface 50. Content from the prerecorded source may be requested by the patient via the patient interface 50. Alternatively, via a control on the assistant interface 94, the assistant may cause content from the prerecorded source to be played on the patient interface 50.

The assistant interface 94 includes an assistant input device 22 and an assistant display 24, which may be collectively called an assistant user interface 22, 24. The assistant input device 22 may include one or more of a telephone, a keyboard, a mouse, a trackpad, or a touch screen, for example. Alternatively or additionally, the assistant input device 22 may include one or more microphones. In some embodiments, the one or more microphones may take the form of a telephone handset, headset, or wide-area microphone or microphones configured for the assistant to speak to a patient via the patient interface 50. In some embodiments, assistant input device 22 may be configured to provide voice-based functionalities, with hardware and/or software configured to interpret spoken instructions by the assistant by using the one or more microphones. The assistant input device 22 may include functionality provided by or similar to existing voice-based assistants such as Siri by Apple, Alexa by Amazon, Google Assistant, or Bixby by Samsung. The assistant input device 22 may include other hardware and/or software components. The assistant input device 22 may include one or more general purpose devices and/or special-purpose devices.

The assistant display 24 may take one or more different forms including, for example, a computer monitor or display screen on a tablet, a smartphone, or a smart watch. The assistant display 24 may include other hardware and/or software components such as projectors, virtual reality capabilities, or augmented reality capabilities, etc. The assistant display 24 may incorporate various different visual, audio, or other presentation technologies. For example, the assistant display 24 may include a non-visual display, such as an audio signal, which may include spoken language and/or other sounds such as tones, chimes, melodies, and/or compositions, which may signal different conditions and/or directions. The assistant display 24 may comprise one or more different display screens presenting various data and/or interfaces or controls for use by the assistant. The assistant display 24 may include graphics, which may be presented by a web-based interface and/or by a computer program or application (App.).

In some embodiments, the system 10 may provide computer translation of language from the assistant interface 94 to the patient interface 50 and/or vice-versa. The computer translation of language may include computer translation of spoken language and/or computer translation of text. Additionally or alternatively, the system 10 may provide voice recognition and/or spoken pronunciation of text. For example, the system 10 may convert spoken words to printed text and/or the system 10 may audibly speak language from printed text. The system 10 may be configured to recognize spoken words by any or all of the patient, the clinician, and/or the assistant. In some embodiments, the system 10 may be configured to recognize and react to spoken requests or commands by the patient. For example, the system 10 may automatically initiate a telemedicine session in response to a verbal command by the patient (which may be given in any one of several different languages).

In some embodiments, the server 30 may generate aspects of the assistant display 24 for presentation by the assistant interface 94. For example, the server 30 may include a web server configured to generate the display screens for presentation upon the assistant display 24. For example, the artificial intelligence engine 11 may generate recommended optimal treatment plans and/or excluded treatment plans for patients and generate the display screens including those recommended optimal treatment plans and/or ruled-out treatment plans for presentation on the assistant display 24 of the assistant interface 94. In some embodiments, the assistant display 24 may be configured to present a virtualized desktop hosted by the server 30. In some embodiments, the server 30 may be configured to communicate with the assistant interface 94 via the first network 34. In some embodiments, the first network 34 may include a local area network (LAN), such as an Ethernet network. In some embodiments, the first network 34 may include the Internet, and communications between the server 30 and the assistant interface 94 may be secured via privacy enhancing technologies, such as, for example, by using encryption over a virtual private network (VPN). Alternatively or additionally, the server 30 may be configured to communicate with the assistant interface 94 via one or more networks independent of the first network 34 and/or other communication means, such as a direct wired or wireless communication channel. In some embodiments, the patient interface 50 and the treatment apparatus 70 may each operate from a patient location geographically separate from a location of the assistant interface 94. For example, the patient interface 50 and the treatment apparatus 70 may be used as part of an in-home rehabilitation system, which may be aided remotely by using the assistant interface 94 at a centralized location, such as a clinic or a call center.

In some embodiments, the assistant interface 94 may be one of several different terminals (e.g., computing devices) that may be grouped together, for example, in one or more call centers or at one or more clinicians' offices. In some embodiments, a plurality of assistant interfaces 94 may be distributed geographically. In some embodiments, a person may work as an assistant remotely from any conventional office infrastructure. Such remote work may be performed, for example, where the assistant interface 94 takes the form of a computer and/or telephone. This remote work functionality may allow for work-from-home arrangements that may include part time and/or flexible work hours for an assistant.

Figure 2:
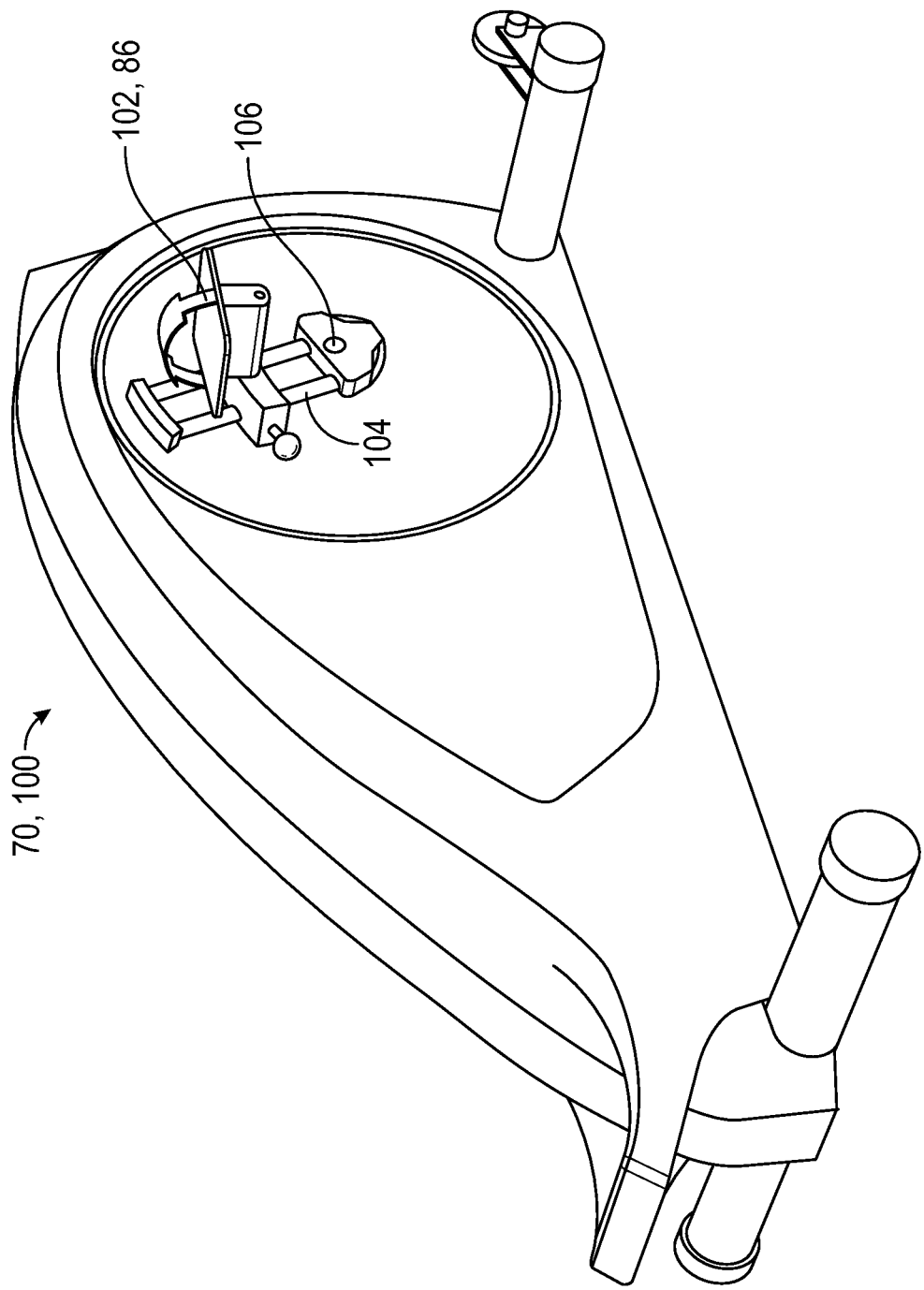
FIG. 2 shows a perspective view of an embodiment of a treatment apparatus according to the present disclosure.
Figure 3:
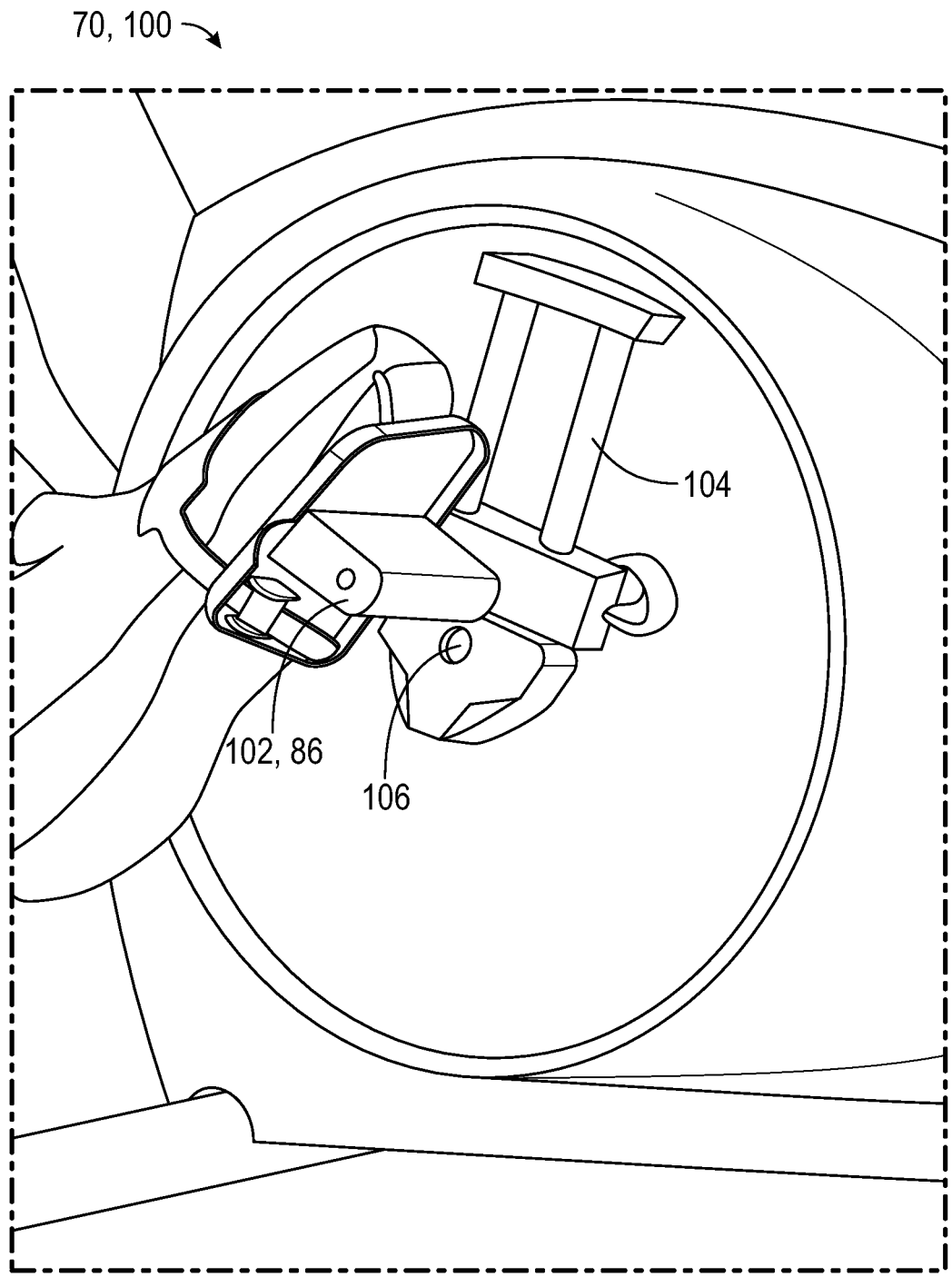
FIG. 3 shows a perspective view of a pedal of the treatment apparatus of FIG. 2 according to the present disclosure.

FIGS. 2-3 show an embodiment of a treatment apparatus 70. More specifically, FIG. 2 shows a treatment apparatus 70 in the form of a stationary cycling machine 100, which may be called a stationary bike, for short. The stationary cycling machine 100 includes a set of pedals 102 each attached to a pedal arm 104 for rotation about an axle 106. In some embodiments, and as shown in FIG. 2, the pedals 102 are movable on the pedal arms 104 in order to adjust a range of motion used by the patient in pedaling. For example, the pedals being located inwardly toward the axle 106 corresponds to a smaller range of motion than when the pedals are located outwardly away from the axle 106. A pressure sensor 86 is attached to or embedded within one of the pedals 102 for measuring an amount of force applied by the patient on the pedal 102. The pressure sensor 86 may communicate wirelessly to the treatment apparatus 70 and/or to the patient interface 50.

Figure 4:
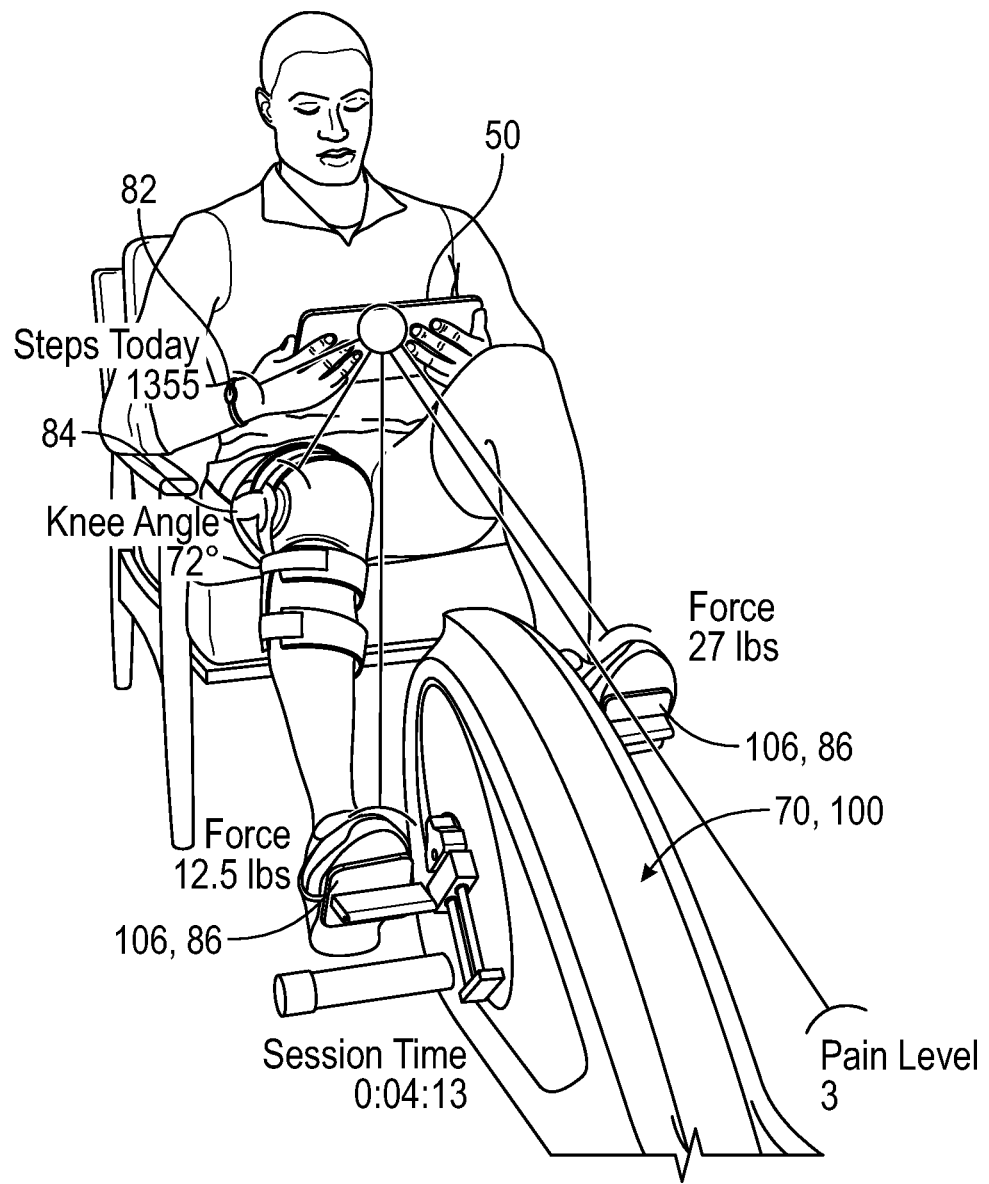
FIG. 4 shows a perspective view of a person using the treatment apparatus of FIG. 2 according to the present disclosure.

FIG. 4 shows a person (a patient) using the treatment apparatus of FIG. 2, and showing sensors and various data parameters connected to a patient interface 50. The example patient interface 50 is a tablet computer or smartphone, or a phablet, such as an iPad, an iPhone, an Android device, or a Surface tablet, which is held manually by the patient. In some other embodiments, the patient interface 50 may be embedded within or attached to the treatment apparatus 70. FIG. 4 shows the patient wearing the ambulation sensor 82 on his wrist, with a note showing "STEPS TODAY 1355", indicating that the ambulation sensor 82 has recorded and transmitted that step count to the patient interface 50. FIG. 4 also shows the patient wearing the goniometer 84 on his right knee, with a note showing "KNEE ANGLE 72°", indicating that the goniometer 84 is measuring and transmitting that knee angle to the patient interface 50. FIG. 4 also shows a right side of one of the pedals 102 with a pressure sensor 86 showing "FORCE 12.5 lbs.," indicating that the right pedal pressure sensor 86 is measuring and transmitting that force measurement to the patient interface 50. FIG. 4 also shows a left side of one of the pedals 102 with a pressure sensor 86 showing "FORCE 27 lbs.", indicating that the left pedal pressure sensor 86 is measuring and transmitting that force measurement to the patient interface 50. FIG. 4 also shows other patient data, such as an indicator of "SESSION TIME 0:04:13", indicating that the patient has been using the treatment apparatus 70 for 4 minutes and 13 seconds. This session time may be determined by the patient interface 50 based on information received from the treatment apparatus 70. FIG. 4 also shows an indicator showing "PAIN LEVEL 3". Such a pain level may be obtained from the patent in response to a solicitation, such as a question, presented upon the patient interface 50.

Figure 5:
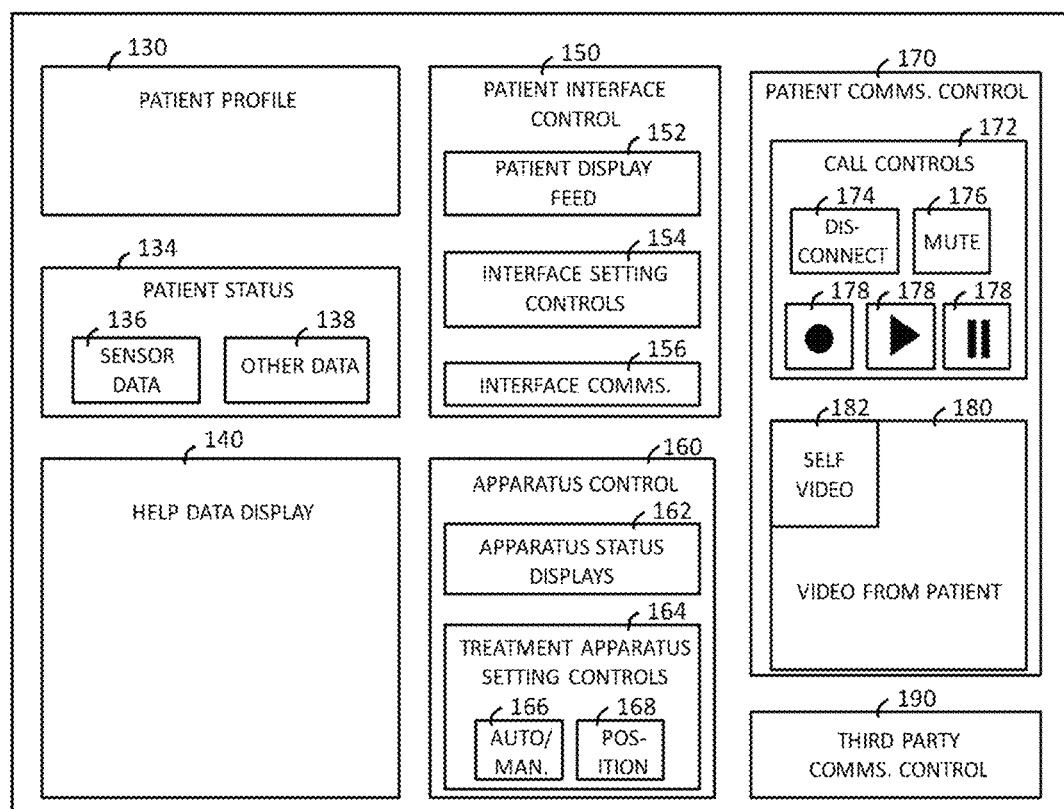
FIG. 5 shows an example embodiment of an overview display of an assistant interface according to the present disclosure.

FIG. 5 is an example embodiment of an overview display 120 of the assistant interface 94. Specifically, the overview display 120 presents several different controls and interfaces for the assistant to remotely assist a patient with using the patient interface 50 and/or the treatment apparatus 70. This remote assistance functionality may also be called telemedicine or telehealth.

Specifically, the overview display 120 includes a patient profile display 130 presenting biographical information regarding a patient using the treatment apparatus 70. The patient profile display 130 may take the form of a portion or region of the overview display 120, as shown in FIG. 5, although the patient profile display 130 may take other forms, such as a separate screen or a popup window. In some embodiments, the patient profile display 130 may include a limited subset of the patient's biographical information. More specifically, the data presented upon the patient profile display 130 may depend upon the assistant's need for that information. For example, a medical professional that is assisting the patient with a medical issue may be provided with medical history information regarding the patient, whereas a technician troubleshooting an issue with the treatment apparatus 70 may be provided with a much more limited set of information regarding the patient. The technician, for example, may be given only the patient's name. The patient profile display 130 may include pseudonymized data and/or anonymized data or use any privacy enhancing technology to prevent confidential patient data from being communicated in a way that could violate patient confidentiality requirements. Such privacy enhancing technologies may enable compliance with laws, regulations, or other rules of governance such as, but not limited to, the Health Insurance Portability and Accountability Act (HIPAA), or the General Data Protection Regulation (GDPR), wherein the patient may be deemed a "data subject".

In some embodiments, the patient profile display 130 may present information regarding the treatment plan for the patient to follow in using the treatment apparatus 70. Such treatment plan information may be limited to an assistant who is a medical professional, such as a doctor or physical therapist. For example, a medical professional assisting the patient with an issue regarding the treatment regimen may be provided with treatment plan information, whereas a technician troubleshooting an issue with the treatment apparatus 70 may not be provided with any information regarding the patient's treatment plan.

In some embodiments, one or more recommended optimal treatment plans and/or ruled-out treatment plans may be presented in the patient profile display 130 to the assistant. The one or more recommended optimal treatment plans and/or ruled-out treatment plans may be generated by the artificial intelligence engine 11 of the server 30 and received from the server 30 in real-time during, inter alia, a telemedicine or telehealth session. An example of presenting the one or more recommended optimal treatment plans and/or ruled-out treatment plans is described below with reference to FIG. 6.

The example overview display 120 shown in FIG. 5 also includes a patient status display 134 presenting status information regarding a patient using the treatment apparatus. The patient status display 134 may take the form of a portion or region of the overview display 120, as shown in FIG. 5, although the patient status display 134 may take other forms, such as a separate screen or a popup window. The patient status display 134 includes sensor data 136 from one or more of the external sensors 82, 84, 86, and/or from one or more internal sensors 76 of the treatment apparatus 70. In some embodiments, the patient status display 134 may present other data 138 regarding the patient, such as last reported pain level, or progress within a treatment plan.

User access controls may be used to limit access, including what data is available to be viewed and/or modified, on any or all of the user interfaces 20, 50, 90, 92, 94 of the system 10. In some embodiments, user access controls may be employed to control what information is available to any given person using the system 10. For example, data presented on the assistant interface 94 may be controlled by user access controls, with permissions set depending on the assistant/user's need for and/or qualifications to view that information.

The example overview display 120 shown in FIG. 5 also includes a help data display 140 presenting information for the assistant to use in assisting the patient. The help data display 140 may take the form of a portion or region of the overview display 120, as shown in FIG. 5. The help data display 140 may take other forms, such as a separate screen or a popup window. The help data display 140 may include, for example, presenting answers to frequently asked questions regarding use of the patient interface 50 and/or the treatment apparatus 70. The help data display 140 may also include research data or best practices. In some embodiments, the help data display 140 may present scripts for answers or explanations in response to patient questions. In some embodiments, the help data display 140 may present flow charts or walk-throughs for the assistant to use in determining a root cause and/or solution to a patient's problem. In some embodiments, the assistant interface 94 may present two or more help data displays 140, which may be the same or different, for simultaneous presentation of help data for use by the assistant. for example, a first help data display may be used to present a troubleshooting flowchart to determine the source of a patient's problem, and a second help data display may present script information for the assistant to read to the patient, such information to preferably include directions for the patient to perform some action, which may help to narrow down or solve the problem. In some embodiments, based upon inputs to the troubleshooting flowchart in the first help data display, the second help data display may automatically populate with script information.

The example overview display 120 shown in FIG. 5 also includes a patient interface control 150 presenting information regarding the patient interface 50, and/or to modify one or more settings of the patient interface 50. The patient interface control 150 may take the form of a portion or region of the overview display 120, as shown in FIG. 5. The patient interface control 150 may take other forms, such as a separate screen or a popup window. The patient interface control 150 may present information communicated to the assistant interface 94 via one or more of the interface monitor signals 98*b*. As shown in FIG. 5, the patient interface control 150 includes a display feed 152 of the display presented by the patient interface 50. In some embodiments, the display feed 152 may include a live copy of the display screen currently being presented to the patient by the patient interface 50. In other words, the display feed 152 may present an image of what is presented on a display screen of the patient interface 50. In some embodiments, the display feed 152 may include abbreviated information regarding the display screen currently being presented by the patient interface 50, such as a screen name or a screen number. The patient interface control 150 may include a patient interface setting control 154 for the assistant to adjust or to control one or more settings or aspects of the patient interface 50. In some embodiments, the patient interface setting control 154 may cause the assistant interface 94 to generate and/or to transmit an interface control signal 98 for controlling a function or a setting of the patient interface 50.

In some embodiments, the patient interface setting control 154 may include collaborative browsing or co-browsing capability for the assistant to remotely view and/or control the patient interface 50. For example, the patient interface setting control 154 may enable the assistant to remotely enter text to one or more text entry fields on the patient interface 50 and/or to remotely control a cursor on the patient interface 50 using a mouse or touchscreen of the assistant interface 94.

In some embodiments, using the patient interface 50, the patient interface setting control 154 may allow the assistant to change a setting that cannot be changed by the patient. For example, the patient interface 50 may be precluded from accessing a language setting to prevent a patient from inadvertently switching, on the patient interface 50, the language used for the displays, whereas the patient interface setting control 154 may enable the assistant to change the language setting of the patient interface 50. In another example, the patient interface 50 may not be able to change a font size setting to a smaller size in order to prevent a patient from inadvertently switching the font size used for the displays on the patient interface 50 such that the display would become illegible to the patient, whereas the patient interface setting control 154 may provide for the assistant to change the font size setting of the patient interface 50.

The example overview display 120 shown in FIG. 5 also includes an interface communications display 156 showing the status of communications between the patient interface 50 and one or more other devices 70, 82, 84, such as the treatment apparatus 70, the ambulation sensor 82, and/or the goniometer 84. The interface communications display 156 may take the form of a portion or region of the overview display 120, as shown in FIG. 5. The interface communications display 156 may take other forms, such as a separate screen or a popup window. The interface communications display 156 may include controls for the assistant to remotely modify communications with one or more of the other devices 70, 82, 84. For example, the assistant may remotely command the patient interface 50 to reset communications with one of the other devices 70, 82, 84, or to establish communications with a new one of the other devices 70, 82, 84. This functionality may be used, for example, where the patient has a problem with one of the other devices 70, 82, 84, or where the patient receives a new or a replacement one of the other devices 70, 82, 84.

The example overview display 120 shown in FIG. 5 also includes an apparatus control 160 for the assistant to view and/or to control information regarding the treatment apparatus 70. The apparatus control 160 may take the form of a portion or region of the overview display 120, as shown in FIG. 5. The apparatus control 160 may take other forms, such as a separate screen or a popup window. The apparatus control 160 may include an apparatus status display 162 with information regarding the current status of the apparatus. The apparatus status display 162 may present information communicated to the assistant interface 94 via one or more of the apparatus monitor signals 99b. The apparatus status display 162 may indicate whether the treatment apparatus 70 is currently communicating with the patient interface 50. The apparatus status display 162 may present other current and/or historical information regarding the status of the treatment apparatus 70.

The apparatus control 160 may include an apparatus setting control 164 for the assistant to adjust or control one or more aspects of the treatment apparatus 70. The apparatus setting control 164 may cause the assistant interface 94 to generate and/or to transmit an apparatus control signal 99 for changing an operating parameter of the treatment apparatus 70, (e.g., a pedal radius setting, a resistance setting, a target RPM, etc.). The apparatus setting control 164 may include a mode button 166 and a position control 168, which may be used in conjunction for the assistant to place an actuator 78 of the treatment apparatus 70 in a manual mode, after which a setting, such as a position or a speed of the actuator 78, can be changed using the position control 168. The mode button 166 may provide for a setting, such as a position, to be toggled between automatic and manual modes. In some embodiments, one or more settings may be adjustable at any time, and without having an associated auto/manual mode. In some embodiments, the assistant may change an operating parameter of the treatment apparatus 70, such as a pedal radius setting, while the patient is actively using the treatment apparatus 70. Such "on the fly" adjustment may or may not be available to the patient using the patient interface 50. In some embodiments, the apparatus setting control 164 may allow the assistant to change a setting that cannot be changed by the patient using the patient interface 50. For example, the patient interface 50 may be precluded from changing a preconfigured setting, such as a height or a tilt setting of the treatment apparatus 70, whereas the apparatus setting control 164 may provide for the assistant to change the height or tilt setting of the treatment apparatus 70.

The example overview display 120 shown in FIG. 5 also includes a patient communications control 170 for controlling an audio or an audiovisual communications session with the patient interface 50. The communications session with the patient interface 50 may comprise a live feed from the assistant interface 94 for presentation by the output device of the patient interface 50. The live feed may take the form of an audio feed and/or a video feed. In some embodiments, the patient interface 50 may be configured to provide two-way audio or audiovisual communications with a person using the assistant interface 94. Specifically, the communications session with the patient interface 50 may include bidirectional (two-way) video or audiovisual feeds, with each of the patient interface 50 and the assistant interface 94 presenting video of the other one. In some embodiments, the patient interface 50 may present video from the assistant interface 94, while the assistant interface 94 presents only audio or the assistant interface 94 presents no live audio or visual signal from the patient interface 50. In some embodiments, the assistant interface 94 may present video from the patient interface 50, while the patient interface 50 presents only audio or the patient interface 50 presents no live audio or visual signal from the assistant interface 94.

In some embodiments, the audio or an audiovisual communications session with the patient interface 50 may take place, at least in part, while the patient is performing the rehabilitation regimen upon the body part. The patient communications control 170 may take the form of a portion or region of the overview display 120, as shown in FIG. 5. The patient communications control 170 may take other forms, such as a separate screen or a popup window. The audio and/or audiovisual communications may be processed and/or directed by the assistant interface 94 and/or by another device or devices, such as a telephone system, or a videoconferencing system used by the assistant while the assistant uses the assistant interface 94. Alternatively or additionally, the audio and/or audiovisual communications may include communications with a third party. For example, the system 10 may enable the assistant to initiate a 3-way conversation regarding use of a particular piece of hardware or software, with the patient and a subject matter expert, such as a medical professional or a specialist. The example patient communications control 170 shown in FIG. 5 includes call controls 172 for the assistant to use in managing various aspects of the audio or audiovisual communications with the patient. The call controls 172 include a disconnect button 174 for the assistant to end the audio or audiovisual communications session. The call controls 172 also include a mute button 176 to temporarily silence an audio or audiovisual signal from the assistant interface 94. In some embodiments, the call controls 172 may include other features, such as a hold button (not shown). The call controls 172 also include one or more record/playback controls 178, such as record, play, and pause buttons to control, with the patient interface 50, recording and/or playback of audio and/or video from the teleconference session. The call controls 172 also include a video feed display 180 for presenting still and/or video images from the patient interface 50, and a self-video display 182 showing the current image of the assistant using the assistant interface. The self-video display 182 may be presented as a picture-in-picture format, within a section of the video feed display 180, as shown in FIG. 5. Alternatively or additionally, the self-video display 182 may be presented separately and/or independently from the video feed display 180.

The example overview display 120 shown in FIG. 5 also includes a third party communications control 190 for use in conducting audio and/or audiovisual communications with a third party. The third party communications control 190 may take the form of a portion or region of the overview display 120, as shown in FIG. 5. The third party communications control 190 may take other forms, such as a display on a separate screen or a popup window. The third party communications control 190 may include one or more controls, such as a contact list and/or buttons or controls to contact a third party regarding use of a particular piece of hardware or software, e.g., a subject matter expert, such as a medical professional or a specialist. The third party communications control 190 may include conference calling capability for the third party to simultaneously communicate with both the assistant via the assistant interface 94, and with the patient via the patient interface 50. For example, the system 10 may provide for the assistant to initiate a 3-way conversation with the patient and the third party.

Figure 6:
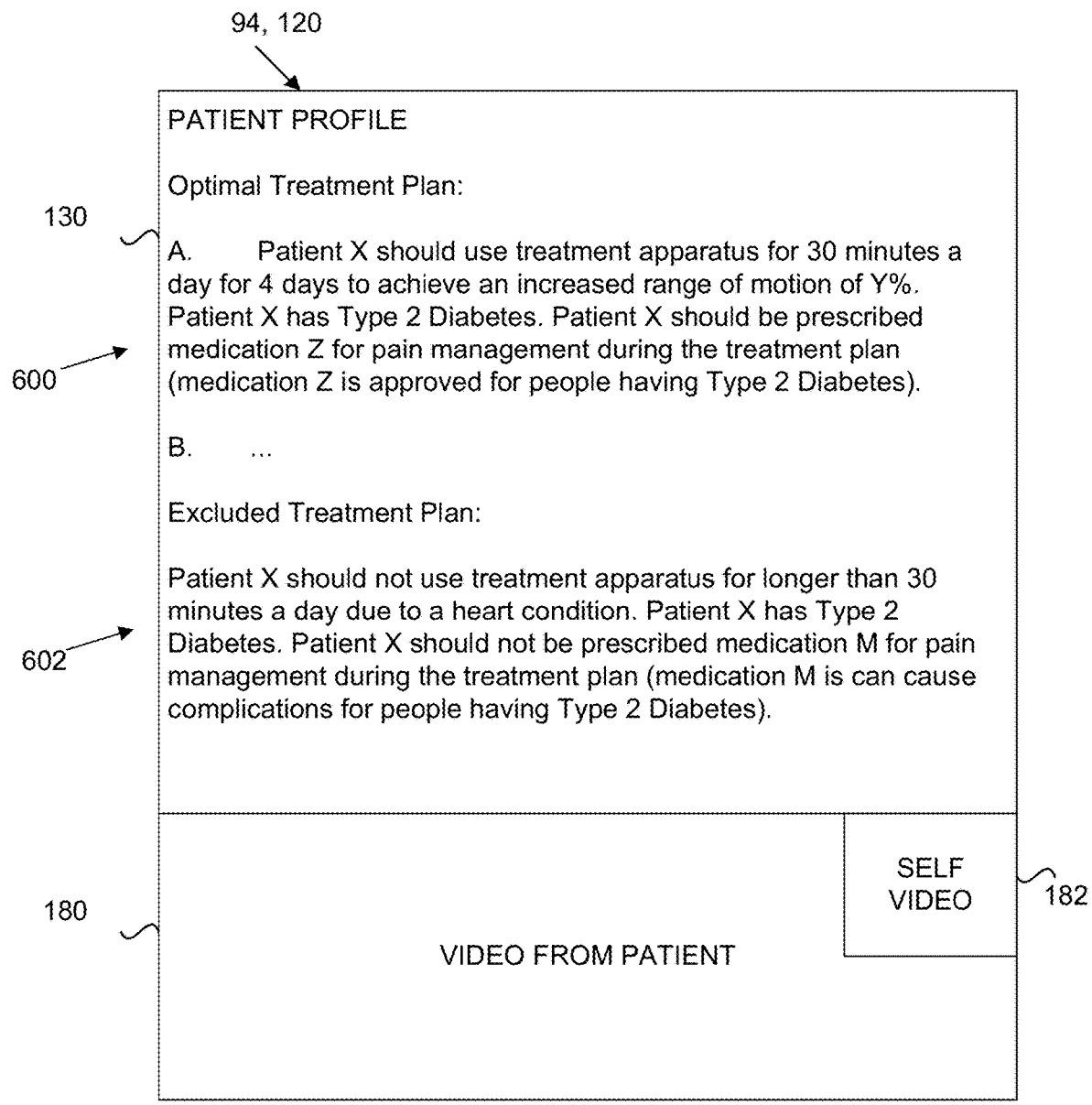
FIG. 6 shows an example embodiment of an overview display of the assistant interface presenting recommended optimal treatment plans and excluded treatment plans in real-time during a telemedicine session according to the present disclosure.

FIG. 6 shows an example embodiment of the overview display 120 of the assistant interface 94 presenting recommended optimal treatment plans and ruled-out treatment plans in real-time during a telemedicine session according to the present disclosure. As depicted, the overview display 120 just includes sections for the patient profile 130 and the video feed display 180, including the self-video display 182. Any suitable configuration of controls and interfaces of the overview display 120 described with reference to FIG. 5 may be presented in addition to or instead of the patient profile 130, the video feed display 180, and the self-video display 182.

The assistant (e.g., medical professional), who is using the assistant interface 94 (e.g., computing device) during the telemedicine session, may be presented in the self-video 182 in a portion of the overview display 120 (e.g., user interface presented on a display screen 24 of the assistant interface 94) that also presents a video from the patient in the video feed display 180. As depicted, another portion of the overview display 120 includes the patient profile display 130.

The patient profile display 130 is presenting two example optimal treatment plans 600 and one example excluded treatment plan 602. As described herein, the optimal treatment plans may be recommended in view of various clinical information and characteristics of the patient being treated. The clinical information may include information pertaining to characteristics of other people, treatment plans followed by the other people, and results of the treatment plans. To generate the recommended optimal treatment plans 600 the patient should follow to achieve a desired result, a pattern between the characteristics of the patient being treated and the other people may be matched by one or more machine learning models 13 of the artificial intelligence engine 11. Each of the recommended optimal treatment plans may be generated based on different desired results.

For example, suppose the following: treatment plan "A" indicates "Patient X should use treatment apparatus for 30 minutes a day for 4 days to achieve an increased range of motion of Y %; Patient X has Type 2 Diabetes; and Patient X should be prescribed medication Z for pain management during the treatment plan (medication Z is approved for people having Type 2 Diabetes)." Accordingly, the optimal treatment plan generated achieves increasing the range of motion of Y %. As may be appreciated, the optimal treatment plan also includes a recommended medication (e.g., medication Z) to prescribe to the patient to manage pain in view of a known medical disease (e.g., Type 2 Diabetes) of the patient. That is, the recommended patient medication not only does not conflict with the medical condition of the patient but thereby improves the probability of a superior patient outcome.

Recommended optimal treatment plan "B" may specify, based on a different desired result of the treatment plan, a different treatment plan including a different treatment protocol for a treatment apparatus, a different medication regimen, etc.

As depicted, the patient profile display 130 may also present the ruled-out treatment plans 602. These types of treatment plans are shown to the assistant using the assistant interface 94 to alert the assistant not to recommend certain portions of a treatment plan to the patient. For example, the ruled-out treatment plan could specify the following: "Patient X should not use treatment apparatus for longer than 30 minutes a day due to a heart condition; Patient X has Type 2 Diabetes; and Patient X should not be prescribed medication M for pain management during the treatment plan (in this scenario, medication M can cause complications for people having Type 2 Diabetes). Specifically, the ruled-out treatment plan points out a limitation of a treatment protocol where, due to a heart condition, Patient X should not exercise for more than 30 minutes a day. The ruled-out treatment plan also points out that Patient X should not be prescribed medication M because it conflicts with the medical condition Type 2 Diabetes.

The assistant may select the optimal treatment plan for the patient on the overview display 120. For example, the assistant may use an input peripheral (e.g., mouse, touchscreen, microphone, keyboard, etc.) to select from the optimal treatment plans 600 for the patient. In some embodiments, during the telemedicine session, the assistant may discuss the pros and cons of the recommended optimal treatment plans 600 with the patient.

In any event, the assistant may select the optimal treatment plan for the patient to follow to achieve the desired result. The selected optimal treatment plan may be transmitted to the patient interface 50 for presentation. The patient may view the selected optimal treatment plan on the patient interface 50. In some embodiments, the assistant and the patient may discuss during the telemedicine session the details (e.g., treatment protocol using treatment apparatus 70, diet regimen, medication regimen, etc.) in real-time.

FIG. 7 shows an example embodiment of a server 30 translating clinical information 700 into a medical description language 702 for processing by an artificial intelligence engine 11 according to the present disclosure. The clinical information 700 may be written by a person having a certain professional credential, license, or degree. In the depicted example, the clinical information 700 includes a portion of meta-analyses for a clinical trial titled "EFFECT OF USING TREATMENT PLAN FOR HIP OSTEOARTHRITIS PAIN". The portion includes a section for "Results" and a section for "Conclusion". There may be many other portions (e.g., details of the trial procedure, biographies of subjects, etc.) of the clinical information 700 that, for clarity of explanation, are not depicted.

One or more machine learning models 13 may be trained to parse a body of structured or unstructured text (e.g., clinical information 700) in search of a corpus of keywords that represent target information. The target information may be included in one or more portions of the clinical information 700. Target information may refer to any suitable information of interest, such as characteristics of people (e.g., vital signs, medical conditions, medical procedures, allergies, familial medical information, measurements, etc.), treatment plans followed by the people, results of the treatment plans, clinical trial information, treatment apparatuses used for the treatment plan, and the like.

Using tags representing the target information and values associated with the tags, the one or more machine learning models 13 may generate a canonical format defined by the medical descriptive language. The values may be numbers, characters, alphanumeric characters, strings, arrays, and the like, wherein they are obtained from the portions of the clinical information 700 (including the target information). The target information may be organized in parent-child relationships based on the structure, organization, and/or relationships of the information. For example, the keyword "Results" may be identified and determined to be a parent level tag due to its encompassing children target information, such as trials, subjects, treatment plan, treatment apparatus, subject characteristics, and conclusions. As such, a parent-level tag for "" may include child-level tags for "<trials>", "<subjects>", "<treatment plan>", "<treatment apparatus>", "<subject characteristics>", and "<conclusions>". Each tag may have a corresponding ending tag (e.g., " . . . ").

An embodiment of operations which a trained machine learning model 13 performs to encode the portion of clinical information 700 in the medical description language 702 is now discussed. The trained machine learning model 13 identified keywords "treatment plan" and "treatment apparatus" in the portion of the clinical information 700. Once identified, the trained machine learning model 13 may analyze words in the vicinity (e.g., to the left and right) of the keywords to determine, based on training data, whether the words match a recognized context. The trained machine learning model 13 may also determine, based on training data and based on attributes of the data, whether the words are recognized as being associated with the keywords. In FIG. 7, the trained machine learning model may determine the words "range of motion (ROM)" fit the context of the keyword "treatment apparatus" and also are likely recognizable as being associated with the keyword "treatment apparatus". Accordingly, the value "ROM" is placed in between tags "<treatment apparatus>" and "</treatment apparatus>" representing target information. The other tags representing target information in the canonical format of the medical description language 702 may be populated in a similar manner. The medical description language 702 representing the portion of the clinical information 700 may be saved in the patient data store 44 in an appropriate patient cohort-equivalent database.

Figure 8:
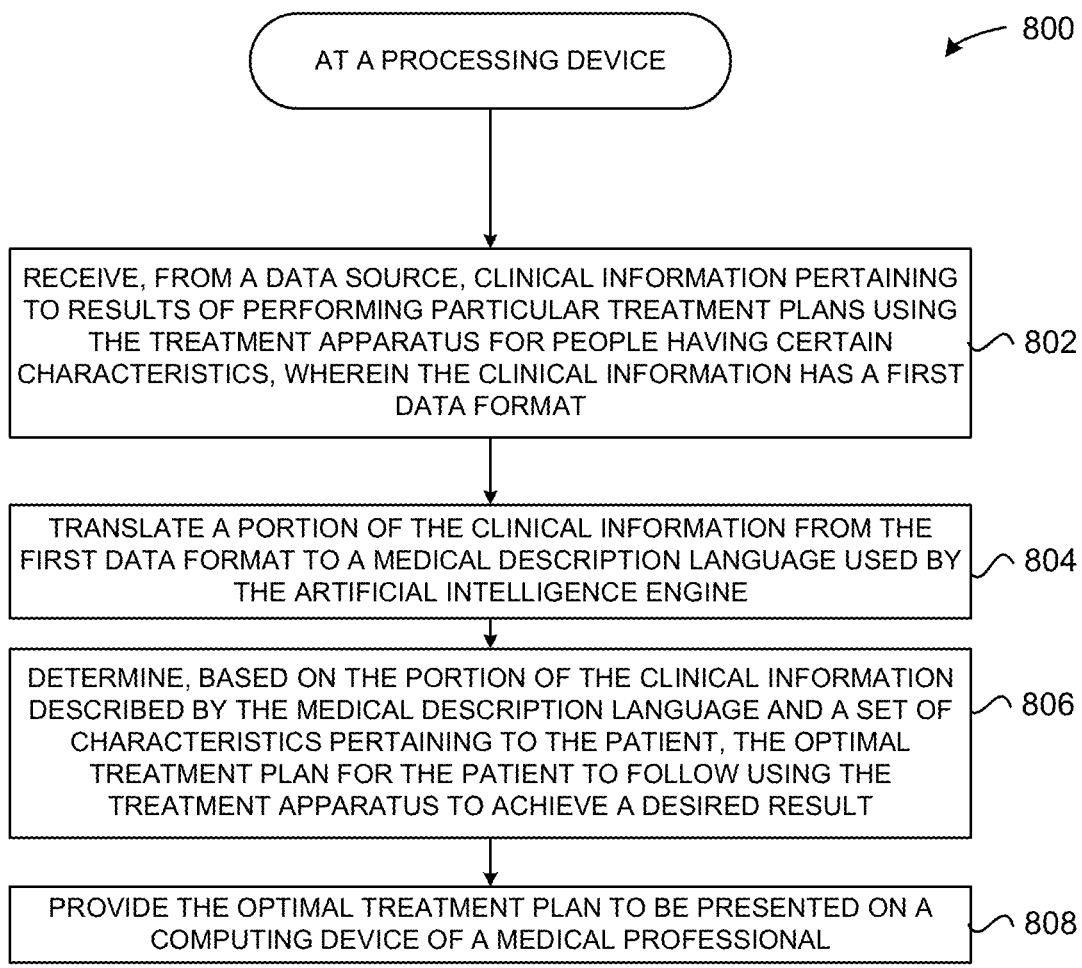
FIG. 8 shows an example embodiment of a method for recommending an optimal treatment plan according to the present disclosure.

FIG. 8 shows an example embodiment of a method 800 for recommending an optimal treatment plan according to the present disclosure. The method 800 is performed by processing logic that may include hardware (circuitry, dedicated logic, etc.), software (such as is run on a general-purpose computer system or a dedicated machine), or a combination of both. The method 800 and/or each of its individual functions, routines, subroutines, or operations may be performed by one or more processors of a computing device (e.g., any component of FIG. 1, such as server 30 executing the artificial intelligence engine 11). In certain implementations, the method 800 may be performed by a single processing thread. Alternatively, the method 800 may be performed by two or more processing threads, each thread implementing one or more individual functions, routines, subroutines, or operations of the methods.

For simplicity of explanation, the method 800 is depicted and described as a series of operations. However, operations in accordance with this disclosure can occur in various orders and/or concurrently, and/or with other operations not presented and described herein. For example, the operations depicted in the method 800 may occur in combination with any other operation of any other method disclosed herein. Furthermore, not all illustrated operations may be required to implement the method 800 in accordance with the disclosed subject matter. In addition, those skilled in the art will understand and appreciate that the method 800 could alternatively be represented as a series of interrelated states via a state diagram or events.

At 802, the processing device may receive, from a data source 15, clinical information 700 pertaining to results of performing particular treatment plans using the treatment apparatus 70 for people having certain characteristics. The clinical information has a first data format, which may include natural language text in the form of words arranged in sentences that are further arranged in paragraphs. The first data format may be a report or description, wherein the report or description may include information pertaining to clinical trials, medical research, meta-analyses, evidence-based guidelines, journals, and the like. The first data format may include information arranged in an unstructured manner and may have a first data size (e.g., bytes, kilobytes, etc.).

The certain characteristics of the people may include medications prescribed to the people, injuries of the people, medical procedures performed on the people, measurements of the people, allergies of the people, medical conditions of the people, first historical information of the people, vital signs of the people, symptoms of the people, familial medical information of the people, or some combination thereof. The characteristics may also include the following information pertaining to the people: demographic, geographic, diagnostic, measurement- or test-based, medically historic, etiologic, cohort-associative, differentially diagnostic, surgical, physically therapeutic, pharmacologic and other treatment(s) recommended.

At 804, the processing device may translate a portion of the clinical information from the first data format to a medical description language 702 used by the artificial intelligence engine 11. The medical description language 702 may include a second data format that structures the unstructured data of the clinical information 700. For example, the medical description language 702 may include using tag-value pairs, where the tags identify the type of value stored between the tags. The medical description language 702 may have a second data size (e.g., bits) that is smaller than the first data size of the clinical information 700. The medical description language may include telemedical data.

At 806, the processing device may determine, based on the portion of the clinical information 700 described by the medical description language 702 and a set of characteristics pertaining to a patient, the optimal treatment plan 600 for the patient to follow when using the treatment apparatus 70 to achieve a desired result. One or more machine learning models 13 of the artificial intelligence engine 11 may be trained to output the optimal treatment plan 600. For example, one machine learning model 13 may be trained to match a pattern between the portion of the clinical information described by the medical description language 702 with the set of characteristics of the patient. In some embodiments, the set of characteristics of the patient is also represented in the medical description language. The pattern is associated with the optimal treatment plan that may produce the desired result.

In some embodiments, the optimal treatment plan may include information pertaining to a medical procedure to perform on the patient, a treatment protocol for the patient using the treatment apparatus 70, a diet regimen for the patient, a medication regimen for the patient, a sleep regimen for the patient, or some combination thereof.

The desired result may include obtaining a certain result within a certain time period. The certain result may include a range of motion the patient achieves using the treatment apparatus 70, an amount of force exerted by the patient on a portion of the treatment apparatus 70, an amount of time the patient exercises using the treatment apparatus 70, a distance the patient travels using the treatment apparatus 70, a level of pain experienced by the patient when using the treatment apparatus 70, or some combination thereof.

In some embodiments, the processing device may determine, based on the portion of the clinical information described by the medical description language and the set of characteristics pertaining to the patient, a second optimal treatment plan for the patient to follow using the treatment apparatus 70 to achieve a second desired result. The desired result may pertain to a recovery outcome and the second desired result may pertain to a recovery time. The recovery outcome may include achieving a certain threshold of functionality, mobility movement, range of motion, etc. of a particular body part. The recovery time may include achieving a certain threshold of functionality, mobility, movement, range of motion, etc. of a particular body part within a certain threshold period of time. For example, some people may prefer to recover to a certain level of mobility as fast as possible without full recovery. As discussed above, different machine learning models 13 may be trained, using different clinical information, to provide different recommended treatment plans that may produce different desired results.

In some embodiments, the processing device may determine, based on the portion of the clinical information described by the medical description language and the set of characteristics pertaining to the patient, an excluded treatment plan 602 that should not be recommended for the patient to follow when using the treatment apparatus 70 to achieve the desired result. In some embodiments, as depicted in FIG. 6, the optimal treatment plan(s) 600 and the excluded treatment plan(s) 602 may be concurrently presented in a first portion (e.g., patient profile display 130) of the user interface while at least the video or other multimedia data from the patient engaged in the telemedicine session may be presented in another portion (e.g., video feed display 180).

In some embodiments, the optimal treatment plan(s) 600 and the excluded treatment plan(s) 602 may be concurrently presented while the medical professional is not engaged in a telemedicine session. For example, the optimal treatment plan(s) 600 and the excluded treatment plan(s) 602 may be presented in the user interface before a telemedicine session begins or after a telemedicine session ends.

At 808, the processing device may provide the optimal treatment plan to be presented in a user interface (e.g., overview display 120) on a computing device (e.g., assistant interface 94) of a medical professional. In addition, any other generated optimal treatment plans 600 may be provided to the computing device of the medical professional. For example, different optimal treatment plans that result in different outcomes may be presented to the medical professional. The processing device may receive a selected treatment plan of any of the treatment plans presented. In some embodiments, the medical professional may select the optimal treatment plan based on an outcome preference of the patient. For example, an athlete might wish to optimize for performance, while a retiree might wish to optimize for a pain-free quality of life. The selected treatment plan may be transmitted to the computing device of the patient for presentation on a user interface. In some embodiments, the optimal treatment plan(s) may be provided to the computing device of the medical professional during a telemedicine session to cause the optimal treatment plan to be presented in real-time in a first portion of the user interface while video and, optionally, other multimedia of the patient is concurrently presented in a second portion of the user interface. The selected treatment plan may be presented on the computing device of the patient during the telemedicine session such that the medical professional can explain the selected treatment plan to the patient.

Figure 9:
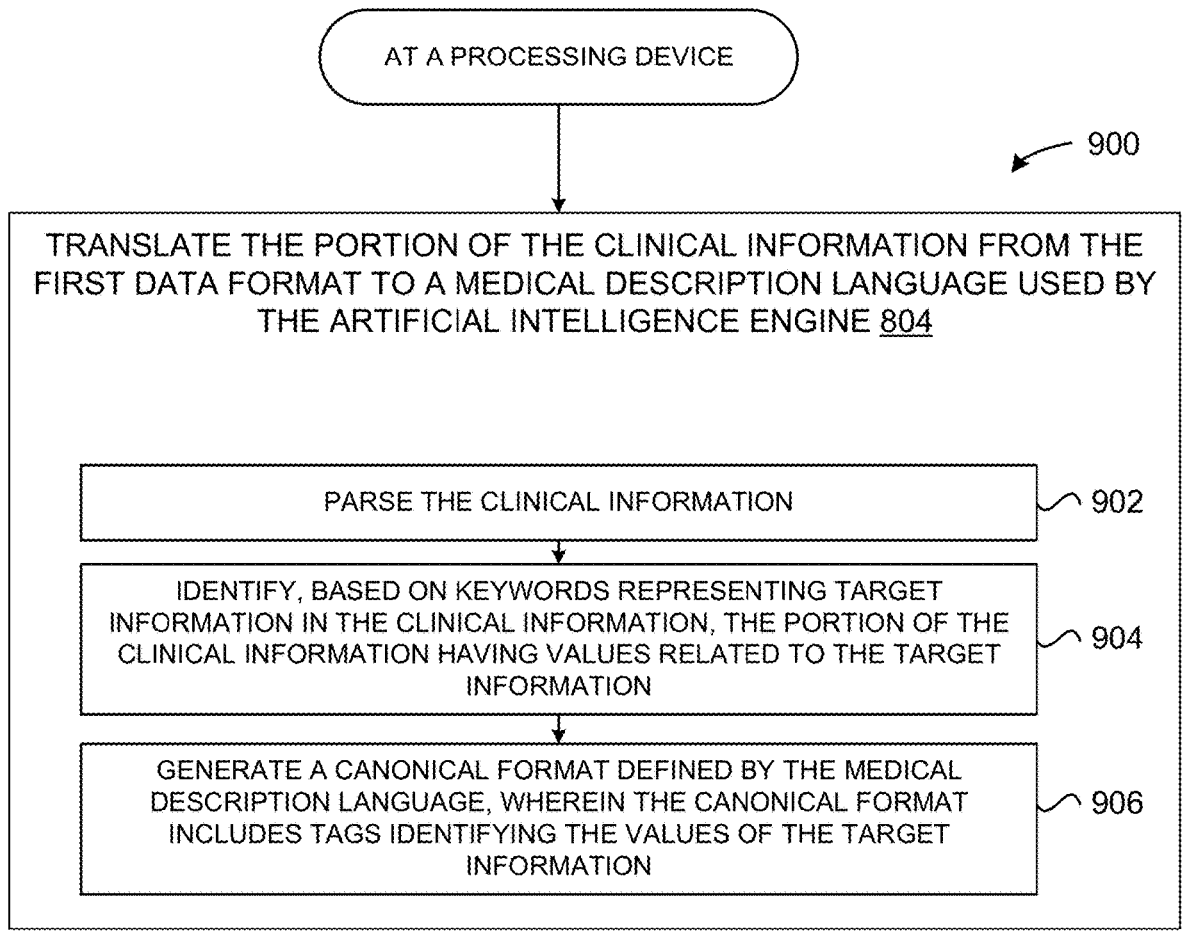
FIG. 9 shows an example embodiment of a method for translating clinical information into the medical description language according to the present disclosure.

FIG. 9 shows an example embodiment of a method 900 for translating clinical information into the medical description language according to the present disclosure. Method 900 includes operations performed by processors of a computing device (e.g., any component of FIG. 1, such as server 30 executing the artificial intelligence engine 11). In some embodiments, one or more operations of the method 900 are implemented in computer instructions stored on a memory device and executed by a processing device. The method 900 may be performed in the same or a similar manner as described above in regard to method 800. The operations of the method 900 may be performed in some combination with any of the operations of any of the methods described herein.

The method 900 may include operation 804 from the previously-described method 800 depicted in FIG. 8. For example, at 804 in the method 600, the processing device may translate a portion of the clinical information from the first data format to a medical description language used by the artificial intelligence engine.

The method 900 in FIG. 9 includes operations 902, 904, and 906. The operations 902, 904, and 906 may be performed by one or more trained machine learning models 13 of the artificial intelligence engine 11.

At 902, the processing device may parse the clinical information. At 904, the processing device may identify, based on keywords representing target information in the clinical information, the portion of the clinical information having values related to the target information. At 906, the processing device may generate a canonical format defined by the medical description language. The canonical format may include tags identifying values of the target information. The tags may be attributes describing specific characteristics of the target information. The specific characteristics may include which cohort class a person is placed in, age of the person, semantic information, being related to a certain cohort, familial history, and the like. In some embodiments, the specific characteristics may include any information or indication that a person is at risk.

The canonical format may enable more efficient processing of the portion of the clinical information represented by the medical description language when training a machine learning model to generate the optimal treatment plans for patients who are using the trained machine learning model. Further, the canonical format may enable more efficient processing by the trained machine learning model when matching patterns between the characteristics of patients and the portion of the clinical information represented by the medical description language.

Figure 10:
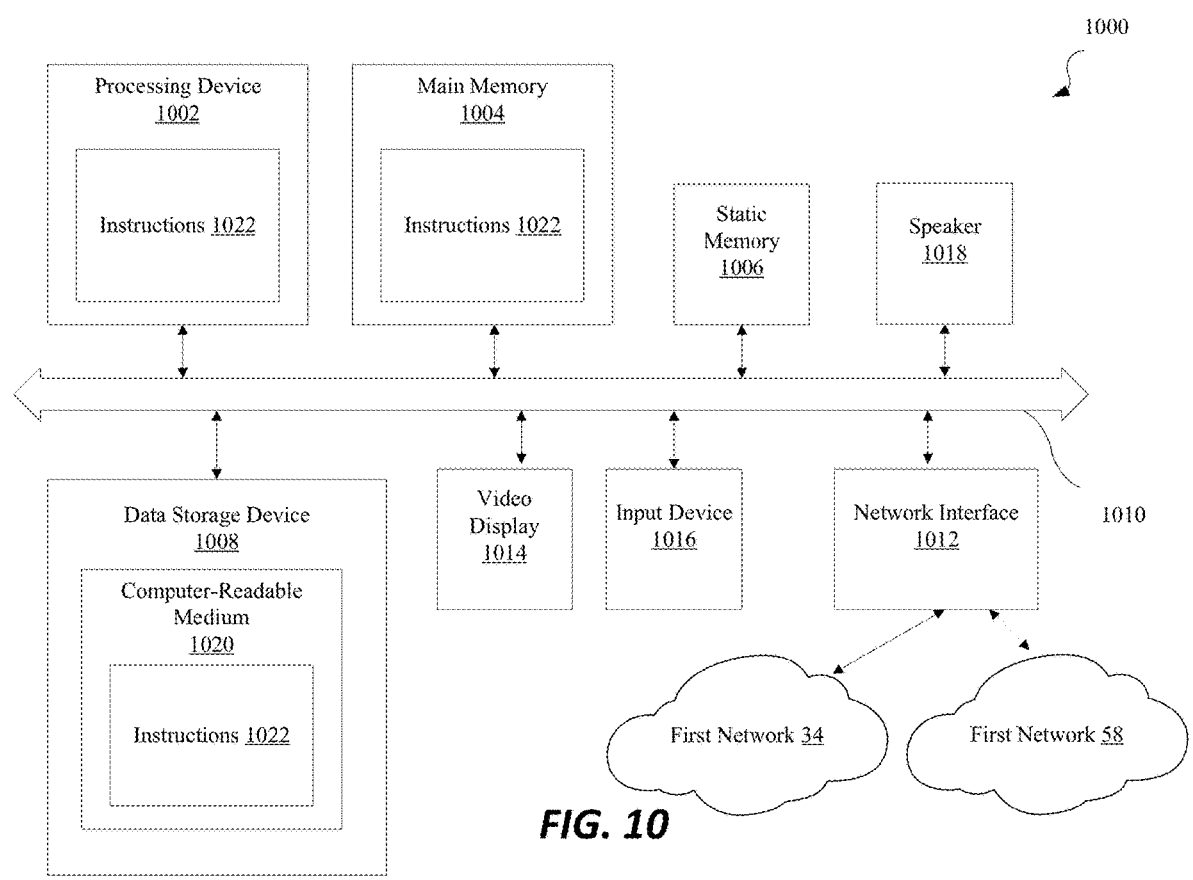
FIG. 10 shows an example computer system according to the present disclosure.

FIG. 10 shows an example computer system 1000 which can perform any one or more of the methods described herein, in accordance with one or more aspects of the present disclosure. In one example, computer system 1000 may include a computing device and correspond to the assistance interface 94, reporting interface 92, supervisory interface 90, clinician interface 20, server 30 (including the AI engine 11), patient interface 50, ambulatory sensor 82, goniometer 84, treatment apparatus 70, pressure sensor 86, or any suitable component of FIG. 1. The computer system 1000 may be capable of executing instructions implementing the one or more machine learning models 13 of the artificial intelligence engine 11 of FIG. 1. The computer system may be connected (e.g., networked) to other computer systems in a LAN, an intranet, an extranet, or the Internet, including via the cloud or a peer-to-peer network. The computer system may operate in the capacity of a server in a client-server network environment. The computer system may be a personal computer (PC), a tablet computer, a wearable (e.g., wristband), a set-top box (STB), a personal Digital Assistant (PDA), a mobile phone, a camera, a video camera, an Internet of Things (IoT) device, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 1000 includes a processing device 1002, a main memory 1004 (e.g., read-only memory (ROM), flash memory, solid state drives (SSDs), dynamic random access memory (DRAM) such as synchronous DRAM (SDRAM)), a static memory 1006 (e.g., flash memory, solid state drives (SSDs), static random access memory (SRAM)), and a data storage device 1008, which communicate with each other via a bus 1010.

Processing device 1002 represents one or more general-purpose processing devices such as a microprocessor, central processing unit, or the like. More particularly, the processing device 1002 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 1402 may also be one or more special-purpose processing devices such as an application specific integrated circuit (ASIC), a system on a chip, a field programmable gate array (FPGA), a digital signal processor (DSP), network processor, or the like. The processing device 1402 is configured to execute instructions for performing any of the operations and steps discussed herein.

The computer system 1000 may further include a network interface device 1012. The computer system 1000 also may include a video display 1014 (e.g., a liquid crystal display (LCD), a light-emitting diode (LED), an organic light-emitting diode (OLED), a quantum LED, a cathode ray tube (CRT), a shadow mask CRT, an aperture grille CRT, a monochrome CRT), one or more input devices 1016 (e.g., a keyboard and/or a mouse or a gaming-like control), and one or more speakers 1018 (e.g., a speaker). In one illustrative example, the video display 1014 and the input device(s) 1016 may be combined into a single component or device (e.g., an LCD touch screen).

The data storage device 1016 may include a computer-readable medium 1020 on which the instructions 1022 embodying any one or more of the methods, operations, or functions described herein is stored. The instructions 1022 may also reside, completely or at least partially, within the main memory 1004 and/or within the processing device 1002 during execution thereof by the computer system 1000. As such, the main memory 1004 and the processing device 1002 also constitute computer-readable media. The instructions 1022 may further be transmitted or received over a network via the network interface device 1012.

While the computer-readable storage medium 1020 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

Clause 1. A method for providing, by an artificial intelligence engine, an optimal treatment plan to use with a treatment apparatus, the method comprising:

receiving, from a data source, clinical information pertaining to results of using the treatment apparatus to perform particular treatment plans for people having certain characteristics, wherein the clinical information has a first data format;

translating a portion of the clinical information from the first data format to a medical description language used by the artificial intelligence engine;

determining, based on the portion of the clinical information described by the medical description language and a plurality of characteristics pertaining to a patient, the optimal treatment plan for the patient to follow using the treatment apparatus to achieve a desired result; and providing the optimal treatment plan to be presented on a computing device of a medical professional.

Clause 2. The method of clause 1, wherein translating the portion of the clinical information from the first data format to the medical description language used by the artificial intelligence engine further comprises:

parsing the clinical information;

identifying, based on keywords representing target information in the clinical information, the portion of the clinical information having values related to the target information;

generating a canonical format defined by the medical description language, wherein the canonical format comprises tags identifying the values of the target information.

Clause 3. The method of clause 2, wherein the tags are attributes describing specific characteristics of the target information;

Clause 4. The method of clause 1, wherein providing the optimal treatment plan to be presented on the computing device of the medical professional further comprises:

causing, during a telemedicine session, the optimal treatment plan to be presented on a user interface of the computing device of the medical professional, wherein the optimal treatment plan is not presented on a display screen of a computing device, such display screen configured to be used by the patient during the telemedicine session.

Clause 5. The method of clause 1, further comprising:

determining, based on the portion of the clinical information described by the medical description language and the plurality of characteristics pertaining to the patient, a ruled-out treatment plan that should not be recommended for the patient to follow when using the treatment apparatus to achieve the desired result; and providing the excluded treatment plan to be presented on the computing device of the medical professional.

Clause 6. The method of clause 1, further comprising:

determining, based on the portion of the clinical information described by the medical description language and the plurality of characteristics pertaining to the patient, a second optimal treatment plan for the patient to follow when using the treatment apparatus to achieve a second desired result, wherein the desired result pertains to a recovery outcome and the second desired result pertains to a recovery time; and providing the second optimal treatment plan to be presented on the computing device of the medical professional;

receiving a selected treatment plan of either the optimal treatment plan or the second optimal treatment plan; and transmitting the selected treatment plan to a computing device of the patient for presenting on a user interface of the computing device of the patient.

Clause 7. The method of clause 1, wherein the desired result comprises obtaining a certain result within a certain time period, and the certain result comprises:

a range of motion the patient achieves using the treatment apparatus, an amount of force exerted by the patient on a portion of the treatment apparatus, an amount of time the patient exercises using the treatment apparatus, a distance the patient travels using the treatment apparatus, or some combination thereof.

Clause 8. The method of clause 1, wherein:

the certain characteristics of the people comprise first medications prescribed to the people, first injuries of the people, first medical procedures performed on the people, first measurements of the people, first allergies of the people, first medical conditions of the people, first historical information of the people, first vital signs of the people, first symptoms of the people, first familial medical information of the people, first demographic information of the people, first geographic information of the people, first measurement-or test-based information of the people, first medically historic information of the people, first etiologic information of the people, first cohort-associative information of the people, first differentially diagnostic information of the people, first surgical information of the people, first physically therapeutic information of the people, first pharmacologic information of the people, first other treatments recommended to the people, or some combination thereof, and the plurality of characteristics of the patient comprise second medications of the patient, second injuries of the patient, second medical procedures performed on the patient, second measurements of the patient, second allergies of the patient, second medical conditions of the patient, second historical information of the patient, second vital signs of the patient, second symptoms of the patient, second familial medical information of the patient, second demographic information of the patient, second geographic information of the patient, second measurement- or test-based information of the patient, second medically historic information of the patient, second etiologic information of the patient, second cohort-associative information of the patient, second differentially diagnostic information of the patient, second surgical information of the patient, second physically therapeutic information of the patient, second pharmacologic information of the patient, second other treatments recommended to the patient, or some combination thereof.

Clause 9. The method of clause 1, wherein the clinical information is written by a person having a certain professional credential and comprises a journal article, a clinical trial, evidence-based guidelines, meta-analysis, or some combination thereof.

Clause 10. The method of clause 1, wherein determining, based on the portion of the clinical information described by the medical description language and the plurality of characteristics pertaining to the patient, the optimal treatment plan for the patient to follow when using the treatment apparatus to achieve the desired result further comprises:

matching a pattern between the portion of the clinical information described by the medical description language with the plurality of characteristics of the patient, wherein the pattern is associated with the optimal treatment plan that leads to the desired result.

Clause 11. The method of clause 1, wherein the optimal treatment plan comprises:

a medical procedure to perform on the patient, a treatment protocol for the patient using the treatment apparatus, a diet regimen for the patient, a medication regimen for the patient, a sleep regimen for the patient, or some combination thereof.

Clause 12. A tangible, non-transitory computer-readable medium storing instructions that, when executed, cause a processing device to:

receive, from a data source, clinical information pertaining to results of using the treatment apparatus to perform particular treatment plans for people having certain characteristics, wherein the clinical information has a first data format;

translate a portion of the clinical information from the first data format to a medical description language used by the artificial intelligence engine;

determine, based on the portion of the clinical information described by the medical description language and a plurality of characteristics pertaining to a patient, the optimal treatment plan for the patient to follow using the treatment apparatus to achieve a desired result; and provide the optimal treatment plan to be presented on a computing device of a medical professional.

Clause 13. The computer-readable medium of clause 12, wherein translating the portion of the clinical information from the first data format to the medical description language used by the artificial intelligence engine further comprises:

parse the clinical information;

identify, based on keywords representing target information in the clinical information, the portion of the clinical information having values of the target information;

generate a canonical format defined by the medical description language, wherein the canonical format comprises tags identifying the values of the target information.

Clause 14. The computer-readable medium of clause 12, wherein providing the optimal treatment plan to be presented on the computing device of the medical professional further comprises:

causing, during a telemedicine session, the optimal treatment plan to be presented on a user interface of the computing device of the medical professional, wherein, during the telemedicine session, the optimal treatment plan is not presented on a user interface of a computing device of the patient.

Clause 15. The computer-readable medium of clause 12, wherein the processing device further:

determines, based on the portion of the clinical information described by the medical description language and the plurality of characteristics pertaining to the patient, a second optimal treatment plan for the patient to follow when using the treatment apparatus to achieve a second desired result, wherein the desired result pertains to a recovery outcome and the second desired result pertains to a recovery time; and provides the second optimal treatment plan to be presented on the computing device of the medical professional;

receives a selected treatment plan of either the optimal treatment plan or the second optimal treatment plan; and transmits the selected treatment plan to a computing device of the patient.

Clause 16. The computer-readable medium of clause 12, wherein the desired result comprises obtaining a certain result within a certain time period, and the certain result comprises:

a range of motion the patient achieves using the treatment apparatus, an amount of force exerted by the patient on a portion of the treatment apparatus, an amount of time the patient exercises using the treatment apparatus, a distance the patient travels using the treatment apparatus, or some combination thereof.

Clause 17. The computer-readable medium of clause 12, wherein:

the certain characteristics of the people comprise first medications prescribed to the people, first injuries of the people, first medical procedures performed on the people, first measurements of the people, first allergies of the people, first medical conditions of the people, first historical information of the people, first vital signs of the people, first symptoms of the people, first familial medical information of the people, first demographic information of the people, first geographic information of the people, first measurement- or test-based information of the people, first medically historic information of the people, first etiologic information of the people, first cohort-associative information of the people, first differentially diagnostic information of the people, first surgical information of the people, first physically therapeutic information of the people, first pharmacologic information of the people, first other treatments recommended to the people, or some combination thereof, and the plurality of characteristics of the patient comprise second medications of the patient, second injuries of the patient, second medical procedures performed on the patient, second measurements of the patient, second allergies of the patient, second medical conditions of the patient, second historical information of the patient, second vital signs of the patient, second symptoms of the patient, second familial medical information of the patient, second demographic information of the patient, second geographic information of the patient, second measurement- or test-based information of the patient, second medically historic information of the patient, second etiologic information of the patient, second cohort-associative information of the patient, second differentially diagnostic information of the patient, second surgical information of the patient, second physically therapeutic information of the patient, second pharmacologic information of the patient, second other treatments recommended to the patient, or some combination thereof.

Clause 18. The computer-readable medium of clause 12, wherein the clinical information is written by a person having a certain professional credential and comprises a journal article, a clinical trial, evidence-based guidelines, or some combination thereof.

Clause 19. A system comprising:

a memory device storing instructions; and a processing device communicatively coupled to the memory device, wherein the processing device executes the instructions to:

receive, from a data source, clinical information pertaining to results of using the treatment apparatus to perform particular treatment plans for people having certain characteristics, wherein the clinical information has a first data format;

translate a portion of the clinical information from the first data format to a medical description language used by the artificial intelligence engine;

determine, based on the portion of the clinical information described by the medical description language and a plurality of characteristics pertaining to a patient, the optimal treatment plan for the patient to follow when using the treatment apparatus to achieve a desired result; and provide the optimal treatment plan to be presented on a computing device of a medical professional.

Clause 20. The system of clause 19, wherein translating the portion of the clinical information from the first data format to the medical description language used by the artificial intelligence engine further comprises:

parse the clinical information;

identify, based on keywords representing target information described by the clinical information, the portion of the clinical information having values of the target information;

generate a canonical format defined by the medical description language, wherein the canonical format comprises tags identifying the values of the target information.

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

The various aspects, embodiments, implementations, or features of the described embodiments can be used separately or in any combination. The embodiments disclosed herein are modular in nature and can be used in conjunction with or coupled to other embodiments.

Consistent with the above disclosure, the examples of assemblies enumerated in the following clauses are specifically contemplated and are intended as a non-limiting set of examples.

What is claimed is:

1. A method for providing, by an artificial intelligence engine, an optimal treatment plan to use with a treatment apparatus, the method comprising:

receiving, from a data source, clinical information pertaining to results of using the treatment apparatus to perform particular treatment plans for people having certain characteristics, wherein the clinical information has a first data format;

translating a portion of the clinical information from the first data format to a medical description language used by the artificial intelligence engine, wherein the translating is performed by a trained machine learning model that performs, based on training data, contextual word analysis to identify target information in the portion of the clinical information and encodes a value of the target information in one or more tags defined by a canonical format of the medical description language;

determining, based on the portion of the clinical information described by the medical description language and a plurality of characteristics pertaining to a patient, the optimal treatment plan for the patient to follow using the treatment apparatus to achieve a desired result; and providing the optimal treatment plan to be presented on a computing device;

receiving a selection of the optimal treatment plan for the patient; and transmitting a signal to the treatment apparatus, and in response to the treatment apparatus receiving the signal, adjusting a portion of the treatment apparatus, such adjustment to comply with an operating parameter specified in the optimal treatment plan.

2. The method of claim 1, wherein translating the portion of the clinical information from the first data format to the medical description language used by the artificial intelligence engine further comprises:

parsing the clinical information;

identifying, based on keywords representing target information in the clinical information, the portion of the clinical information having values related to the target information; and generating the canonical format defined by the medical description language, wherein the canonical format comprises tags identifying the values of the target information.

3. The method of claim 2, wherein the tags are attributes describing specific characteristics of the target information.

4. The method of claim 1, wherein providing the optimal treatment plan to be presented on the computing device of the medical professional further comprises:

causing, during a telemedicine session, the optimal treatment plan to be presented on a user interface of the computing device of the medical professional, wherein the optimal treatment plan is not presented on a display screen of a computing device, such display screen configured to be used by the patient during the telemedicine session.

5. The method of claim 1, further comprising:

determining, based on the portion of the clinical information described by the medical description language and the plurality of characteristics pertaining to the patient, a ruled-out treatment plan that should not be recommended for the patient to follow when using the treatment apparatus to achieve the desired result; and providing the excluded treatment plan to be presented on the computing device of the medical professional.

6. The method of claim 1, further comprising:

determining, based on the portion of the clinical information described by the medical description language and the plurality of characteristics pertaining to the patient, a second optimal treatment plan for the patient to follow when using the treatment apparatus to achieve a second desired result, wherein the desired result pertains to a recovery outcome and the second desired result pertains to a recovery time; and providing the second optimal treatment plan to be presented on the computing device of the medical professional;

receiving a selected treatment plan of either the optimal treatment plan or the second optimal treatment plan; and transmitting the selected treatment plan to a computing device of the patient for presenting on a user interface of the computing device of the patient.

7. The method of claim 1, wherein the desired result comprises obtaining a certain result within a certain time period, and the certain result comprises:

a range of motion the patient achieves using the treatment apparatus, an amount of force exerted by the patient on a portion of the treatment apparatus, an amount of time the patient exercises using the treatment apparatus, a distance the patient travels using the treatment apparatus, or some combination thereof.

8. The method of claim 1, wherein:

the certain characteristics of the people comprise first medications prescribed to the people, first injuries of the people, first medical procedures performed on the people, first measurements of the people, first allergies of the people, first medical conditions of the people, first historical information of the people, first vital signs of the people, first symptoms of the people, first familial medical information of the people, first demographic information of the people, first geographic information of the people, first measurement- or test-based information of the people, first medically historic information of the people, first etiologic information of the people, first cohort-associative information of the people, first differentially diagnostic information of the people, first surgical information of the people, first physically therapeutic information of the people, first pharmacologic information of the people, first other treatments recommended to the people, or some combination thereof, and the plurality of characteristics of the patient comprise second medications of the patient, second injuries of the patient, second medical procedures performed on the patient, second measurements of the patient, second allergies of the patient, second medical conditions of the patient, second historical information of the patient, second vital signs of the patient, second symptoms of the patient, second familial medical information of the patient, second demographic information of the patient, second geographic information of the patient, second measurement- or test-based information of the patient, second medically historic information of the patient, second etiologic information of the patient, second cohort-associative information of the patient, second differentially diagnostic information of the patient, second surgical information of the patient, second physically therapeutic information of the patient, second pharmacologic information of the patient, second other treatments recommended to the patient, or some combination thereof.

9. The method of claim 1, wherein the clinical information is written by a person having a certain professional credential and comprises a journal article, a clinical trial, evidence-based guidelines, meta-analysis, or some combination thereof.

10. The method of claim 1, wherein determining, based on the portion of the clinical information described by the medical description language and the plurality of characteristics pertaining to the patient, the optimal treatment plan for the patient to follow when using the treatment apparatus to achieve the desired result further comprises:

matching a pattern between the portion of the clinical information described by the medical description language with the plurality of characteristics of the patient, wherein the pattern is associated with the optimal treatment plan that leads to the desired result.

11. The method of claim 1, wherein the optimal treatment plan comprises:
- a medical procedure to perform on the patient,
- a treatment protocol for the patient using the treatment apparatus,
- a diet regimen for the patient,
- a medication regimen for the patient,
- a sleep regimen for the patient, or
- some combination thereof.

12. A tangible, non-transitory computer-readable medium storing instructions that, when executed, cause a processing device to:
- receive, from a data source, clinical information pertaining to results of using the treatment apparatus to perform particular treatment plans for people having certain characteristics, wherein the clinical information has a first data format;
- translate a portion of the clinical information from the first data format to a medical description language used by the artificial intelligence engine, wherein the translating is performed by a trained machine learning model that performs, based on training data, contextual word analysis to identify target information in the portion of the clinical information and encodes a value of the target information in one or more tags defined by a canonical format of the medical description language;
- determine, based on the portion of the clinical information described by the medical description language and a plurality of characteristics pertaining to a patient, the optimal treatment plan for the patient to follow using the treatment apparatus to achieve a desired result;
- provide the optimal treatment plan to be presented on a computing device of a medical professional;
- receive a selection of the optimal treatment plan for the patient; and
- transmit a signal to the treatment apparatus, and in response to the treatment apparatus receiving the signal, adjusting a portion of the treatment apparatus, such adjustment to comply with an operating parameter specified in the optimal treatment plan.

13. The computer-readable medium of claim 12, wherein translating the portion of the clinical information from the first data format to the medical description language used by the artificial intelligence engine further comprises:
- parse the clinical information;
- identify, based on keywords representing target information in the clinical information, the portion of the clinical information having values of the target information; and
- generate a canonical format defined by the medical description language, wherein the canonical format comprises tags identifying the values of the target information.

14. The computer-readable medium of claim 12, wherein providing the optimal treatment plan to be presented on the computing device of the medical professional further comprises:
- causing, during a telemedicine session, the optimal treatment plan to be presented on a user interface of the computing device of the medical professional, wherein, during the telemedicine session, the optimal treatment plan is not presented on a user interface of a computing device of the patient.

15. The computer-readable medium of claim 12, wherein the processing device further:
- determines, based on the portion of the clinical information described by the medical description language and the plurality of characteristics pertaining to the patient, a second optimal treatment plan for the patient to follow when using the treatment apparatus to achieve a second desired result, wherein the desired result pertains to a recovery outcome and the second desired result pertains to a recovery time;
- provides the second optimal treatment plan to be presented on the computing device of the medical professional;
- receives a selected treatment plan of either the optimal treatment plan or the second optimal treatment plan; and
- transmits the selected treatment plan to a computing device of the patient.

16. The computer-readable medium of claim 12, wherein the desired result comprises obtaining a certain result within a certain time period, and the certain result comprises:
- a range of motion the patient achieves using the treatment apparatus,
- an amount of force exerted by the patient on a portion of the treatment apparatus,
- an amount of time the patient exercises using the treatment apparatus,
- a distance the patient travels using the treatment apparatus, or
- some combination thereof.

17. The computer-readable medium of claim 12, wherein:
- the certain characteristics of the people comprise first medications prescribed to the people, first injuries of the people, first medical procedures performed on the people, first measurements of the people, first allergies of the people, first medical conditions of the people, first historical information of the people, first vital signs of the people, first symptoms of the people, first familial medical information of the people, first demographic information of the people, first geographic information of the people, first measurement- or test-based information of the people, first medically historic information of the people, first etiologic information of the people, first cohort-associative information of the people, first differentially diagnostic information of the people, first surgical information of the people, first physically therapeutic information of the people, first pharmacologic information of the people, first other treatments recommended to the people, or some combination thereof, and
- the plurality of characteristics of the patient comprise second medications of the patient, second injuries of the patient, second medical procedures performed on the patient, second measurements of the patient, second allergies of the patient, second medical conditions of the patient, second historical information of the patient, second vital signs of the patient, second symptoms of the patient, second familial medical information of the patient, second demographic information of the patient, second geographic information of the patient, second measurement- or test-based information of the patient, second medically historic information of the patient, second etiologic information of the patient, second cohort-associative information of the patient, second differentially diagnostic information of the patient, second surgical information of the patient, second physically therapeutic information of the patient, second pharmacologic information of the patient, second other treatments recommended to the patient, or some combination thereof.

18. The computer-readable medium of claim 12, wherein the clinical information is written by a person having a certain professional credential and comprises a journal article, a clinical trial, evidence-based guidelines, or some combination thereof.

19. A system comprising:
- a memory device storing instructions; and
- a processing device communicatively coupled to the memory device, wherein the processing device executes the instructions to:
  - receive, from a data source, clinical information pertaining to results of using the treatment apparatus to perform particular treatment plans for people having certain characteristics, wherein the clinical information has a first data format;
  - translate a portion of the clinical information from the first data format to a medical description language used by the artificial intelligence engine, wherein the translating is performed by a trained machine learning model that performs, based on training data, contextual word analysis to identify target information in the portion of the clinical information and encodes a value of the target information in one or more tags defined by a canonical format of the medical description language;
  - determine, based on the portion of the clinical information described by the medical description language and a plurality of characteristics pertaining to a patient, the optimal treatment plan for the patient to follow when using the treatment apparatus to achieve a desired result;
  - provide the optimal treatment plan to be presented on a computing device of a medical professional;
  - receive a selection of the optimal treatment plan for the patient; and
  - transmit a signal to the treatment apparatus, and in response to the treatment apparatus receiving the signal, adjusting a portion of the treatment apparatus, such adjustment to comply with an operating parameter specified in the optimal treatment plan.

20. The system of claim 19, wherein translating the portion of the clinical information from the first data format to the medical description language used by the artificial intelligence engine further comprises:
- parse the clinical information;
- identify, based on keywords representing target information described by the clinical information, the portion of the clinical information having values of the target information; and
- generate a canonical format defined by the medical description language, wherein the canonical format comprises tags identifying the values of the target information.

* * * * *